United States Patent
Hale et al.

(10) Patent No.: US 11,451,912 B1
(45) Date of Patent: Sep. 20, 2022

(54) SYSTEM, METHOD AND COMPUTER PROGRAM PRODUCT FOR THREE-DIMENSIONAL (3D) COMPUTER-AIDED MANUFACTURING (CAM) OF HEARING PROTECTION AND/OR NOISE REDUCTION EAR APPLIANCE

(71) Applicant: LOCKHEED MARTIN CORPORATION, Bethesda, MD (US)

(72) Inventors: Michael W. Hale, Fort Worth, TX (US); Matthew S. Richardson, Fort Worth, TX (US)

(73) Assignee: LOCKHEED MARTIN CORPORATION, Bethesda, MD (US)

( * ) Notice: Subject to any disclaimer, the term of this patent is extended or adjusted under 35 U.S.C. 154(b) by 522 days.

(21) Appl. No.: 16/594,149

(22) Filed: Oct. 7, 2019

(51) Int. Cl.
*H04R 25/00* (2006.01)
*H04R 1/10* (2006.01)
(Continued)

(52) U.S. Cl.
CPC ............ *H04R 25/658* (2013.01); *A61F 11/08* (2013.01); *G06F 30/00* (2020.01); *H04R 1/1016* (2013.01); *H04R 25/652* (2013.01); *A61F 11/085* (2022.01)

(58) Field of Classification Search
CPC ........ A61F 11/08; A61F 11/085; G06F 30/00; H04R 25/658; H04R 1/1016; H04R 25/652
See application file for complete search history.

(56) References Cited

U.S. PATENT DOCUMENTS 8,032,337 B2 * 10/2011 Deichmann .......... H04R 25/652
381/328
8,332,061 B2 12/2012 Baloch et al.
(Continued)

FOREIGN PATENT DOCUMENTS

CN 104224443 12/2014

OTHER PUBLICATIONS

Kovacs, L. et al., "Accuracy and Precision of the Three-Dimensional Assessment of the Facial Surface Using a 3-D Laser Scanner," IEEE Transactions on Medical Imaging, vol. 25, No. 6, Jun. 2006.
(Continued)

*Primary Examiner* — Brian Ensey
(74) *Attorney, Agent, or Firm* — Foley & Lardner LLP

(57) ABSTRACT

A system comprising a scanner to scan an ear and a processor to receive, from the scanner, a non-manifold three-dimensional (3D) digital surface model (DSM) scan data representative of a non-manifold 3D surface model of the auditory canal and the concha of the ear. The 3D surface model is an outer boundary surface for an earpiece appliance. The processor determines an extrema boundary located at a free edge of the 3D surface model; recognizes anatomical features including a cymba concha and auditory canal peak; modifies the 3D surface model relative to the anatomical features by creating a base boundary plane for the appliance, offset some distance from the extrema boundary; creates a closed volume within and between the outer boundary surface, the extrema boundary and the base boundary plane to form a solid 3D earpiece appliance; and causes a computer-aided manufacturing device to manufacture the solid 3D earpiece appliance.

19 Claims, 21 Drawing Sheets

(51) Int. Cl.
　　　*A61F 11/08*　　　(2006.01)
　　　*G06F 30/00*　　　(2020.01)

(56) References Cited

U.S. PATENT DOCUMENTS

| | | | |
|---|---|---|---|
| 8,897,458 B2 | 11/2014 | Parkins et al. | |
| 10,122,989 B2 * | 11/2018 | Fei | A61B 5/1079 |
| 2017/0305040 A1 * | 10/2017 | Schreiner | H04R 25/652 |

OTHER PUBLICATIONS

Lei, J. et al., "Automatic Ear Landmark Localization, Segmentation, and Pose Classification in Range Images," IEEE Transactions on Systems, Man, and Cybernetics: Systems, vol. 46, No. 2, Feb. 2016.

Reichinger, A. et al., "Evaluation of Methods for Optical 3-D Scanning of Human Pinnas," IEEE 2013 International Conference on 3D Vision.

Mafalda, C. et al., "On Producing Customised Soft-Tissue Prostheses Using Digital Tools and Silicone Casting Techniques," IEEE 4th Portuguese BioEngineering Meeting Porto, Portugal, Feb. 26-28, 2015.

Bouchana, A. et al., "Semi-Automatic Algorithm For 3D Volume Reconstruction of Inner Ear Structures Based On CTScan Images," IEEE, 4th International Conference on Advanced Technologies For Signal and Image Processing—ATSIP, Mar. 21-24, 2018, Sousse, Tunisia.

Singare, S. et al., "The Use of Laser Scanner and Rapid Prototyping to Fabricate Auricular Prosthesis," 2010 IEEE, Dongguan Science and Technology Project (2007108101007) and Dongguan Research Development Special Foundation (No. 2006D015).

\* cited by examiner

SYSTEM, METHOD AND COMPUTER PROGRAM PRODUCT FOR THREE-DIMENSIONAL (3D) COMPUTER-AIDED MANUFACTURING (CAM) OF HEARING PROTECTION AND/OR NOISE REDUCTION EAR APPLIANCE

BACKGROUND

Embodiments relate to system, method and computer readable medium for three-dimensional (3D) computer-aided manufacturing (CAM) of hearing protection and/or noise reduction ear appliance.

According to the Centers for Disease Control (CDC), prolonged exposure to any noise above 85 decibels can cause hearing loss. As the exposure level (dBA) increases, there is a time-intensity exchange rate of 3; for every 3 dB increase in noise level, the allowable exposure time is reduced by half.

According to the Department of Veterans Affairs, tinnitus is the most common disability experienced by veterans. Hearing protection devices with consideration toward adequate noise attenuation are used by maintainers and pilots. These hearing protection solutions commonly feature a multi-layer approach with the use of earplugs. Misused and improper non-custom earplugs have been known to result in hearing loss when maintaining and operating loud vehicles and aircraft. Thus, adequate hearing protection helps mitigate the hazards of noise in the workplace.

SUMMARY

Embodiments relate to system, method and computer readable medium for three-dimensional (3D) computer-aided manufacturing (CAM) of hearing protection and/or noise reduction ear appliance. A system comprising a scanner to scan an ear including at least an auditory canal and concha of the ear of a subject; and a computing device having at least one processor and tangible, non-transitory computer readable medium having program instructions which when executed to cause at least one processor to: receive, from the scanner, a non-manifold three-dimensional (3D) digital surface model (DSM) scan data representative of a non-manifold 3D surface model of the auditory canal and the concha of the ear in a computational geometry format, the 3D surface model being an outer boundary surface for an earpiece appliance. The at least one processor further to: determine an extrema boundary located at a free edge of the non-manifold 3D surface model; recognize anatomical features on the non-manifold 3D surface model including a cymba concha and auditory canal peak; and modify the non-manifold 3D surface model relative to the recognized anatomical features by creating a base boundary plane for the earpiece appliance, offset some distance from the extrema boundary. The at least one processor further to: create a closed volume within and between the outer boundary surface, the extrema boundary and the base boundary plane to form a digital data representation of a solid 3D earpiece appliance; and cause a computer-aided manufacturing (CAM) device to manufacture the solid 3D earpiece appliance based on the formed digital data representative of the solid 3D earpiece appliance.

A method comprising receiving, from a scanner device, a non-manifold three-dimensional (3D) digital surface model (DSM) scan data representative of a non-manifold 3D surface model of an auditory canal and a concha of an ear of a subject in a computational geometry format, the 3D surface model being an outer boundary surface for an earpiece appliance; determining an extrema boundary located at a free edge of the non-manifold 3D surface model; recognizing anatomical features on the non-manifold 3D surface model including a cymba concha and auditory canal peak; modifying the non-manifold 3D surface model relative to the recognized anatomical features by creating a base boundary plane for the earpiece appliance, offset some distance from the extrema boundary; creating a closed volume within and between the outer boundary surface, the extrema boundary and the base boundary plane to form a digital data representation of a solid 3D earpiece appliance; and causing a computer-aided manufacturing (CAM) device to manufacture the solid 3D earpiece appliance based on the formed digital data representative of the solid 3D earpiece appliance.

A tangible, non-transitory computer readable medium having instructions stored thereon which when executed to cause at least one processor to: receive, from a scanner, a non-manifold three-dimensional (3D) digital surface model (DSM) scan data representative of a non-manifold 3D surface model of at least an auditory canal and a concha of an ear of a subject in a computational geometry format, the 3D surface model being an outer boundary surface for an earpiece appliance; determine an extrema boundary located at a free edge of the non-manifold 3D surface model; recognize anatomical features on the non-manifold 3D surface model including a cymba concha and auditory canal peak; modify the non-manifold 3D surface model relative to the recognized anatomical features by creating a base boundary plane for the earpiece appliance, offset some distance from the extrema boundary; create a closed volume within and between the outer boundary surface, the extrema boundary and the base boundary plane to form a digital data representation of a solid 3D earpiece appliance; and cause a computer-aided manufacturing (CAM) device to manufacture the solid 3D earpiece appliance based on the formed digital data representative of the solid 3D earpiece appliance.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which.

DETAILED DESCRIPTION

Figure 1:
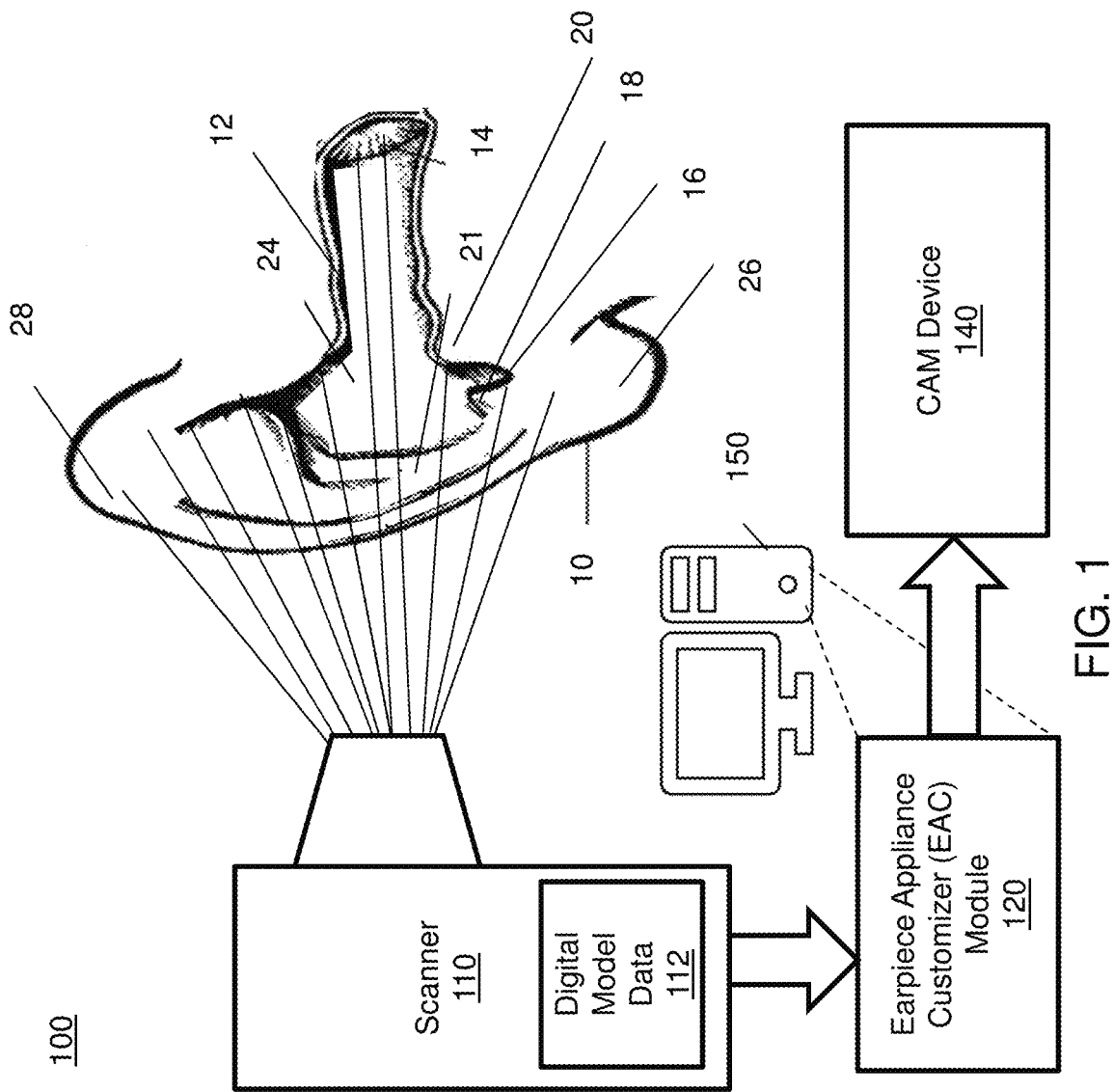
FIG. 1 illustrates a block diagram of a system for three-dimensional (3D) computer-aided manufacturing (CAM) of hearing protection and/or noise reduction ear appliance.

Embodiments are described herein with reference to the attached figures wherein like reference numerals are used throughout the figures to designate similar or equivalent elements. The figures are not drawn to scale and they are provided merely to illustrate aspects disclosed herein. Several disclosed aspects are described below with reference to non-limiting example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. The embodiments are not limited by the illustrated ordering of acts or events, as some acts may occur in different orders and/or concurrently with other acts or events. Furthermore, not all illustrated acts or events are required to implement a methodology in accordance with the embodiments.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

The inventors have determined that the process to create custom earplugs to meet Noise Reduction Rating (NRR) is lengthy and costly. Non-custom earplugs require adequate training to ensure proper use and, even with proper use, may result in hearing loss to service-members with non-compliant auditory canals. Impressions for custom earplugs are performed by service audiologists or contractors.

The inventors have determined that customized earplugs (earpiece appliance) can be remade periodically since the ear's topology of a subject may change over time due to infections, age, weight gain, or other reasons. The non-custom earplugs may be easily available through inventory storage. However, custom earplugs require consistent impression quality, retention of earplug molds, and an infection-controlled lab environment. There may be issues with spares provisioning, as well. The embodiments herein address these issues with a custom-fit, made-to-wear earpiece appliance.

The embodiments are directed to a system with a processor configured to receive three-dimensional (3D) surface model scan data representing an auditory canal and concha from a scanner. The scan data is in a stereolithography (STL), OBJ, a point cloud format, or similar computational geometry format. The processor systematically studies the scan data from the scanner to determine key features (e.g., canal tip, cymba concha tip, and crus of helix) and the surface boundaries of the 3D surface model. A closed volume is created by revising the computational geometry of the scan data by adding the base extension to the computational geometry.

In some embodiments, the base extension may be customized with internal and/or external fastener elements and/or acoustic channels depending on earpiece appliance customization. Thus, the system may further revise the computational geometry until all revisions are complete to form final computational geometry.

Figure 7A:
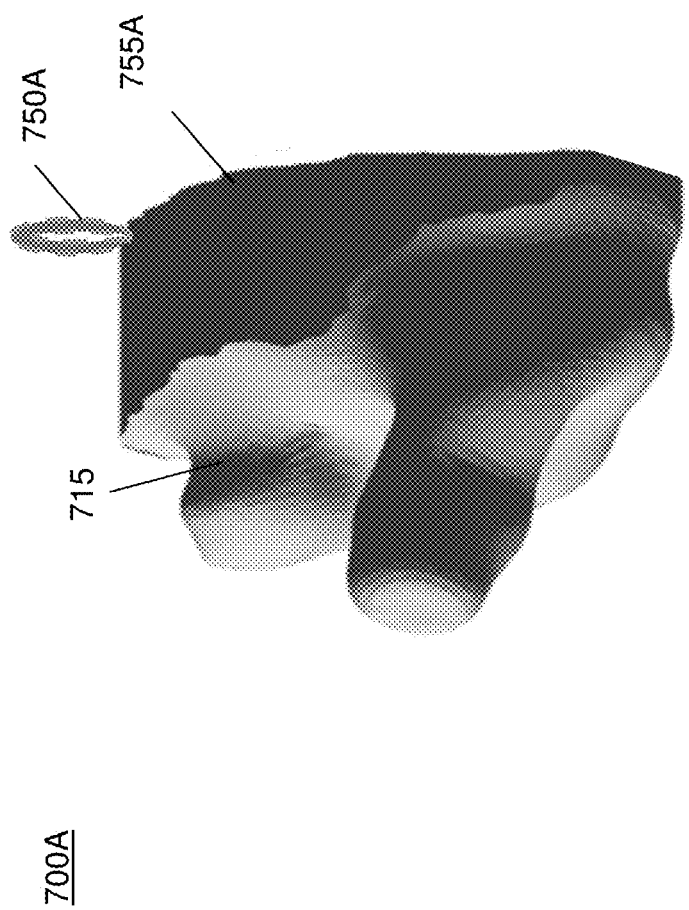
FIG. 7A illustrates a rendered representation of the FIG. 4B computational geometry with external feature.
Figure 7B:
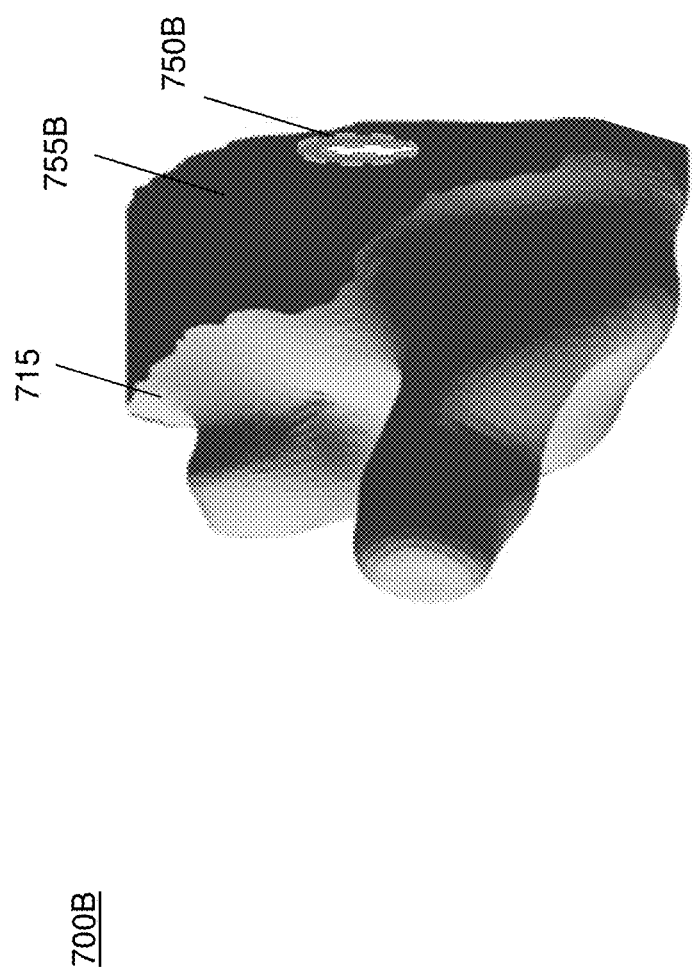
FIG. 7B illustrates a rendered representation of the FIG. 4C computational geometry with internal feature.

In an embodiment where acoustic channels are added, the processor of the system further modifies the revised computational geometry by creating an acoustic channel with other internal and/or external features. This may be done through the use of Boolean operations (union, intersection, and difference) with prefabricated 3D model templates from a feature template database. The finished computational geometry is sent to the CAM device for manufacture of the hearing protection appliance. An acoustic channel is a type of internal feature. FIG. 1 illustrates a block diagram of a system 100 for three-dimensional (3D) computer-aided manufacturing (CAM) of hearing protection and/or noise reduction ear appliance, as seen in FIGS. 7A and 7B, for example. The system 100 may comprise a digital scanner 110 configured to scan an ear 10 (pinna or portion of the pinna) and auditory canal 12 of a subject. The system 100 may include an earpiece appliance customizer (EAC) module 120. The EAC module 120 may be a computer program product stored on tangible and non-transitory computer readable medium, the computer program product when executed causes the generation of a solid earpiece appliance. The solid earpiece appliance may be made of a homogeneous material. By way of non-limiting example, the homogeneous material may be a chemical mixture which is configured to be cured. For example, the homogeneous material may be silicone. The scanner may use a laser scan or a photogrammetry, by way of non-limiting example. The EAC module 120 may include program instructions stored in a computer readable medium which when executed to cause at least one processor of computing device 150 to: receive, from the scanner, digital three-dimensional (3D) surface model scan data representative of the surface of the auditory canal and concha of the ear of the subject; read and store the scan data in a computational geometry format; systematically study the computational geometry format to define key features and surface boundaries, extending, or modifying the base boundary (around the concha) to a defined, selected or predetermined plane, along a common axis; create a closed volume by adding this extension to the computational geometry. The term "modifying" as it relates to the base plane 435 would modify the base plane so that it would end up either above (trim) or below (extend) on the z axis of the base boundary 425.

Figure 3A:
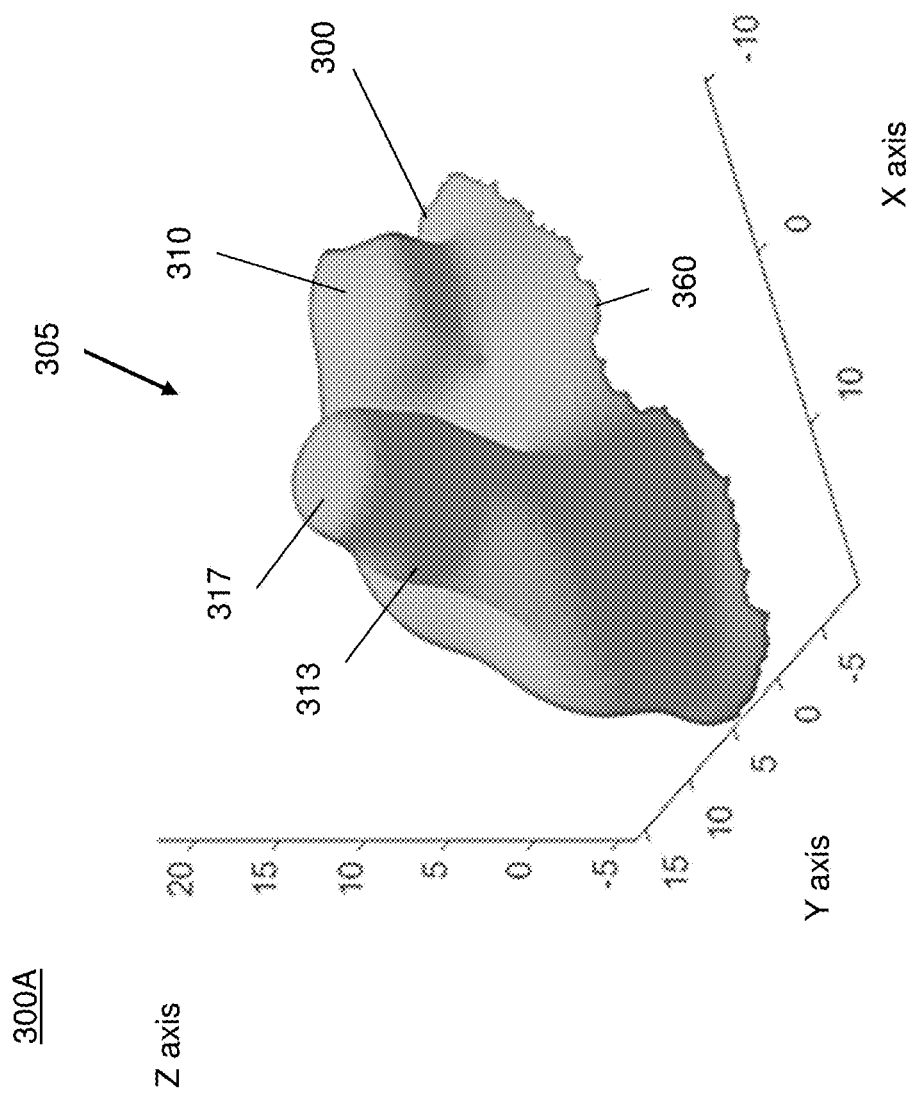
FIG. 3A illustrates a first view of an image representative of a digital surface model of a scanned ear surface.

The term "systematically study" means feature recognition. In other words, the processor of the system is configured to perform feature recognition such as without limitation recognizing the concha (i.e., cymba and cavum) and auditory channel of the ear. The feature recognition may include locating the canal peak 317 (FIG. 3A) or cymba concha peak 310 (FIG. 3A). The features, as shown in FIG. 1, may include one or more of the canal, cymba concha, tragus 20, anti-tragus 18, concha 24 (i.e., cavum), and crus of helix. Other features that may be recognized include one or more of the intertragic notch 16, anti-helix 21 and the lobule 26 (ear lobe). Once the base plane 435 is defined, the surface is segmented, by the processor, into parallel regions (climbing parallel from the base plane) and the maximums of each region (maximum z value) are selected by the processor. This is an example of how the canal peak and the cymba concha peak may be obtained. While this is ongoing, the planar area may be monitored by the processor. Once a change is made from one area to two areas, the climbing continues with two planar sets (e.g., one for the canal, the other tracking vertically up the cymba to obtain the cymba concha peak). Specifically, the climbing or marching along the parallel planes result in a closed cross-section of the volume. The region at which they separate to two closed areas (i.e., canal is separated from the cymba concha) is the crus of helix. The executed EAC module further modifies the revised computational geometry by creating internal and/or external features. The internal features may be at least one of a cavity, a fastener element and an acoustic channel.

The processor of the EAC module 120 may cause computer-aided manufacturing (CAM) device to manufacture the solid 3D earpiece appliance based on the finished computational geometry representative of the solid 3D earpiece appliance. By way of non-limiting example, triangulation methods may be used to revise the computational geometry. For example, a Delaunay Triangulation method may be used on all vertices and to join them together.

The system 100 may include a computer-aided manufacturing (CAM) machine 140 configured, by computer aid, to manufacture a three-dimensional (3D) custom earpiece appliance.

The digital scanner 110 may use digital scanning technology configured to collect a plurality of data points to make a digital map of the ear including the auditory canal and concha. The digital scanner 110 may be configured to create a digital surface model of a subject's one-of-a-kind ear(s). The digital scanner 110 may be a peripheral device interfaced with the computing device 150. In some embodiments, the digital scanner 110 may be remote from the computing device 150 and include its own processor and program code instructions. Digital scanner 110 may employ one of: a laser, ultrasound, or flexible membrane.

The system 100 may be configured to capture a digital representation of the ear from the scanner and automatically interrogate the data associated with the ear to recognize features of the interior shape of the cavity. The system 100 may be configured to modify automatically the interrogated digital representation to produce a printable digital representation of the earpiece appliance.

The system may be configured to automatically modify the printable digital representation of the earplug to include a cavity and positive retention features to captivate electronic components for the purpose of active hearing protection. The system may be configured to capture automatically and send the printable digital representation of the earpiece appliance to the CAM machine, such as a 3D Printer.

FIG. 3A illustrates a first view of an image representative of a digital surface model 300A of a scanned ear surface 305 with a contour representative of the cymba concha peak 310 and auditory canal 313. In order to manufacture an earpiece appliance with a homogeneous material, a solid model needs to be generated using the scanned ear surface 305 having a cymba concha peak 310, acoustic channel 313 and canal peak 317.

Figure 3B:
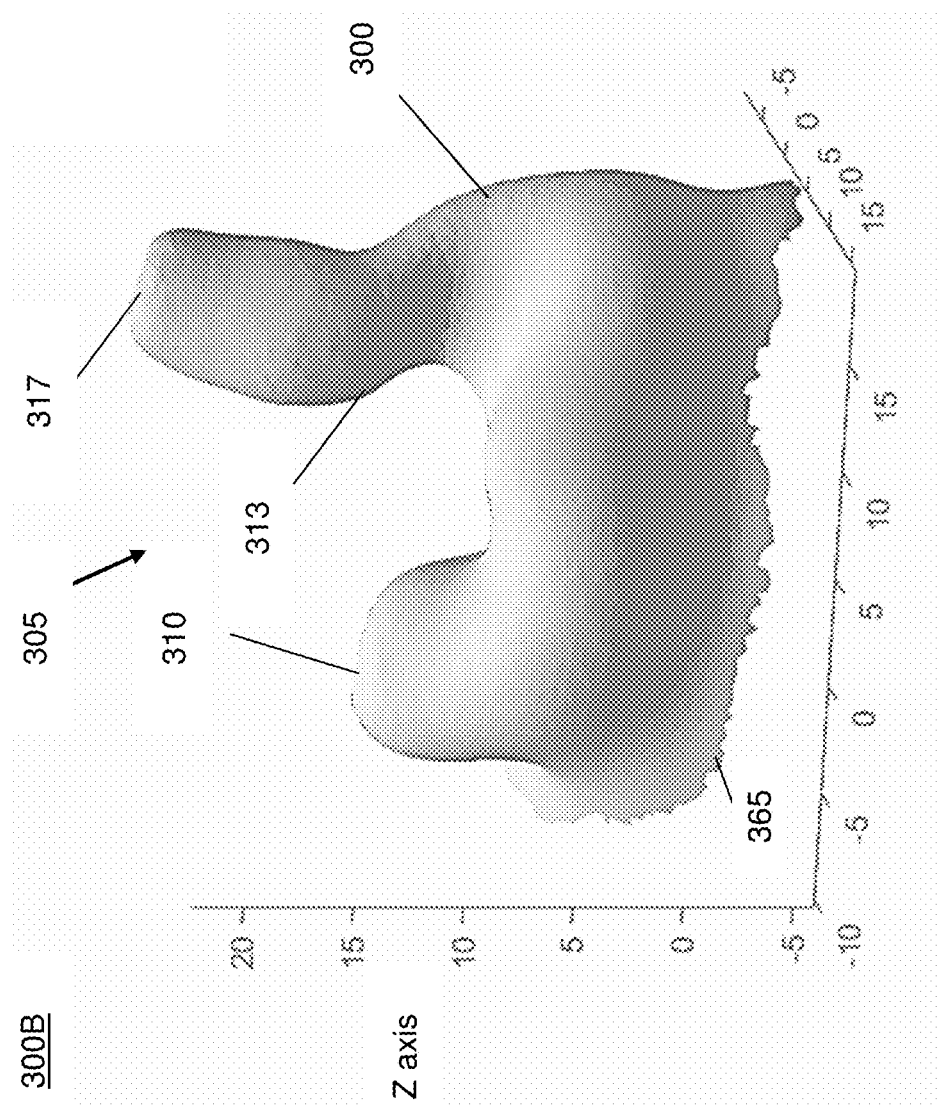
FIG. 3B illustrates a second view of the image representative of a digital surface model of a scanned ear surface, from a different point of view than FIG. 3A.

FIG. 3B illustrates a second view of the image representative of a digital model 300B of a scanned ear surface 305 with a contour representative of the cymba concha peak 310 and auditory canal 313. Digital models 300A and 300B are different views of the same pinna or portion of the pinna of a subject ear. Therefore, reference to digital surface model 300A or digital surface model 300B represents a single digital surface model 300 of the pinna or portion of the same ear.

In order to manufacture an earpiece appliance with a homogeneous material, a solid model needs to be generated using the scanned ear surface 305 having a cymba concha peak 310, acoustic channel 313 and canal peak 317. The term canal peak corresponds to the anatomical location of the tympanic membrane within the auditory canal.

The customizer (EAC) module 120 may be in communication wired or wirelessly with the scanner 110 to receive the digital model data 112 of the ear. The EAC module 120 is configured to incorporate internal and/or external features of one of a passive hearing protection earpiece appliance and an active noise reduction earpiece appliance, as will be described in more detail later. The customizer (EAC) module 120 may be configured to generate an earpiece appliance which may be incorporated into a hearing protection kit.

The CAM device 140 may be configured for direct printing in biocompatible, soft materials (e.g., silicone).

Figure 2A:
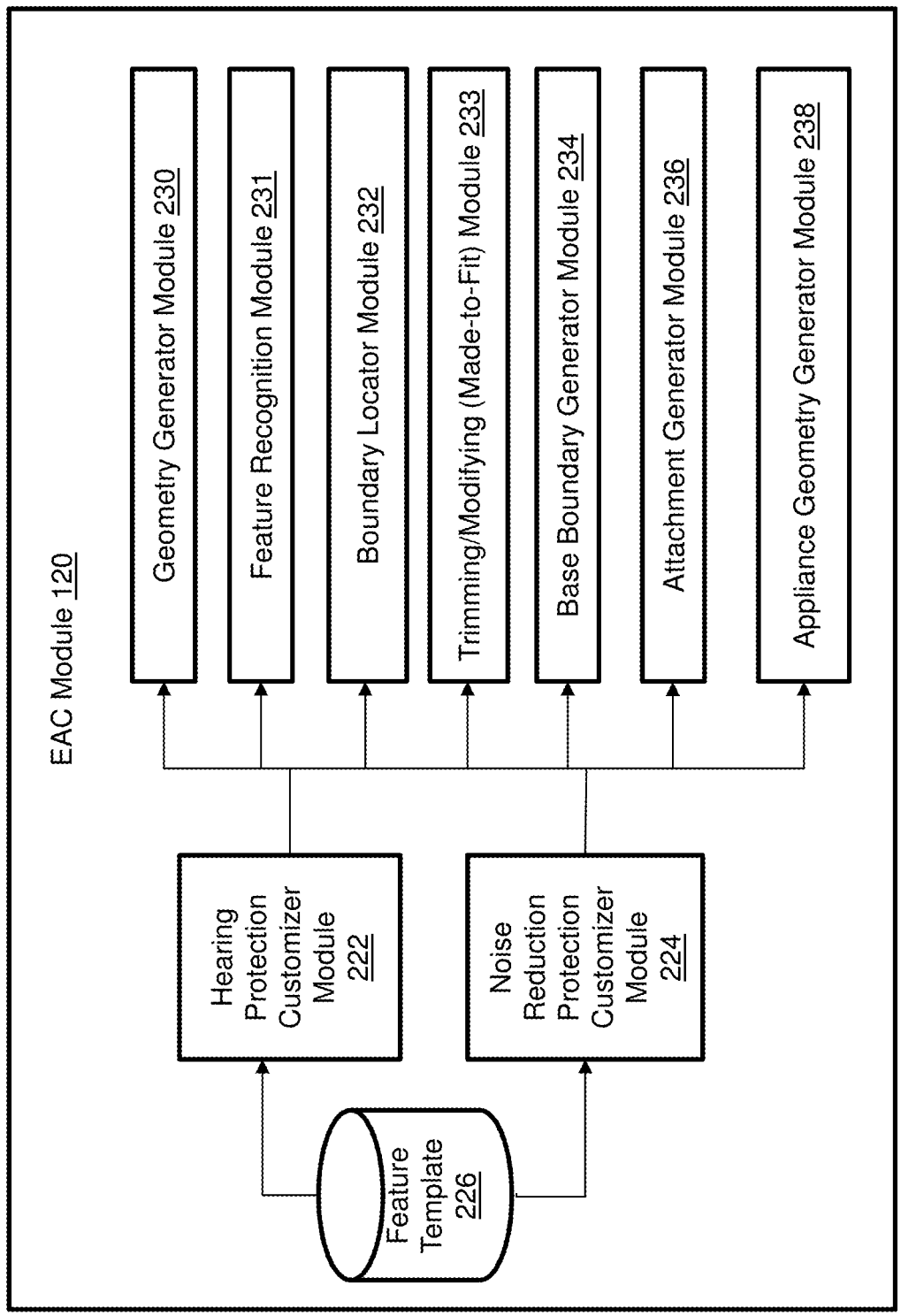
FIG. 2A illustrates a block diagram of an earpiece appliance customizer module.

FIG. 2A illustrates a block diagram of an earpiece appliance customizer (EAC) module 120. The operation of the EAC module 120 will be described in relation to FIG. 2B in combination with FIGS. 3, 4A-4D, 5A-5C, 6, 7A and 7B. The blocks of the method 200 may be performed in the order shown or a different order. One or more of the blocks may be performed contemporaneously. The method 200 may include additional blocks and some blocks may be deleted.

Figure 2B:
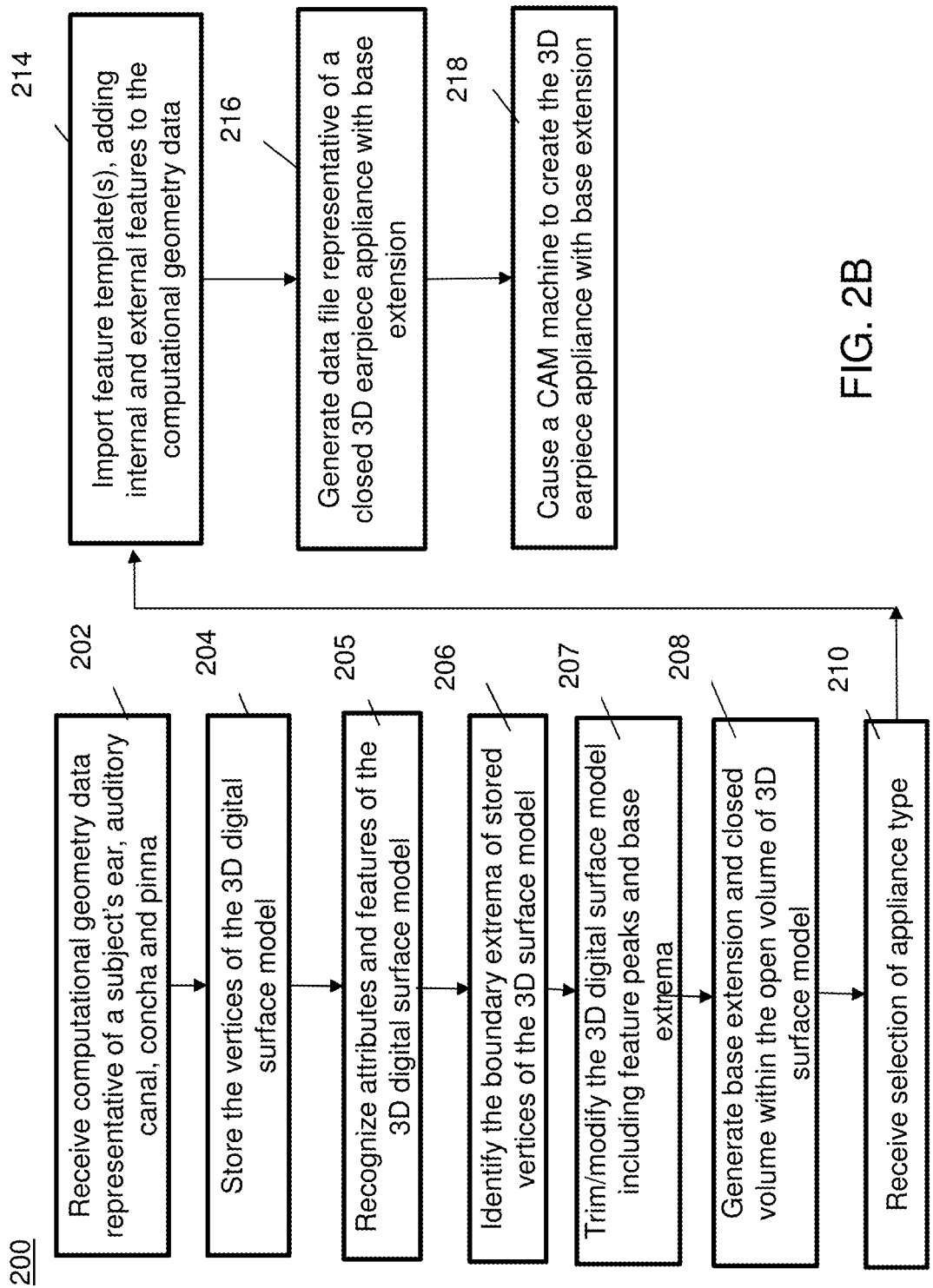
FIG. 2B illustrates a flowchart of manufacturing a made-to-fit earpiece appliance.

The method 200 of FIG. 2B may include, at block 202, receiving a 3D digital model 300 (FIGS. 3A and 3B) of the subject's ear, including the pinna and auditory canal. The scanned portion of the pinna is limited to the front of the ear not to extend past the lower limit of lobule (ear lobe) and the upper limit of the pinna or auricle. FIGS. 3A and 3B illustrate images representative of a scanned 3D ear surface 305 of digital surface model 300 as seen from two different views. The 3D digital model 300 represent a model of the ear's concha and auditory canal. The 3D digital model 300 of FIGS. 3A and 3B is represented in an X, Y, Z coordinate system having an X-axis, Y-axis and Z-axis. The scan data is in an STL, OBJ, point cloud, or similar computational geometry format. The scan data is a non-manifold 3D digital surface model.

Figure 4A:
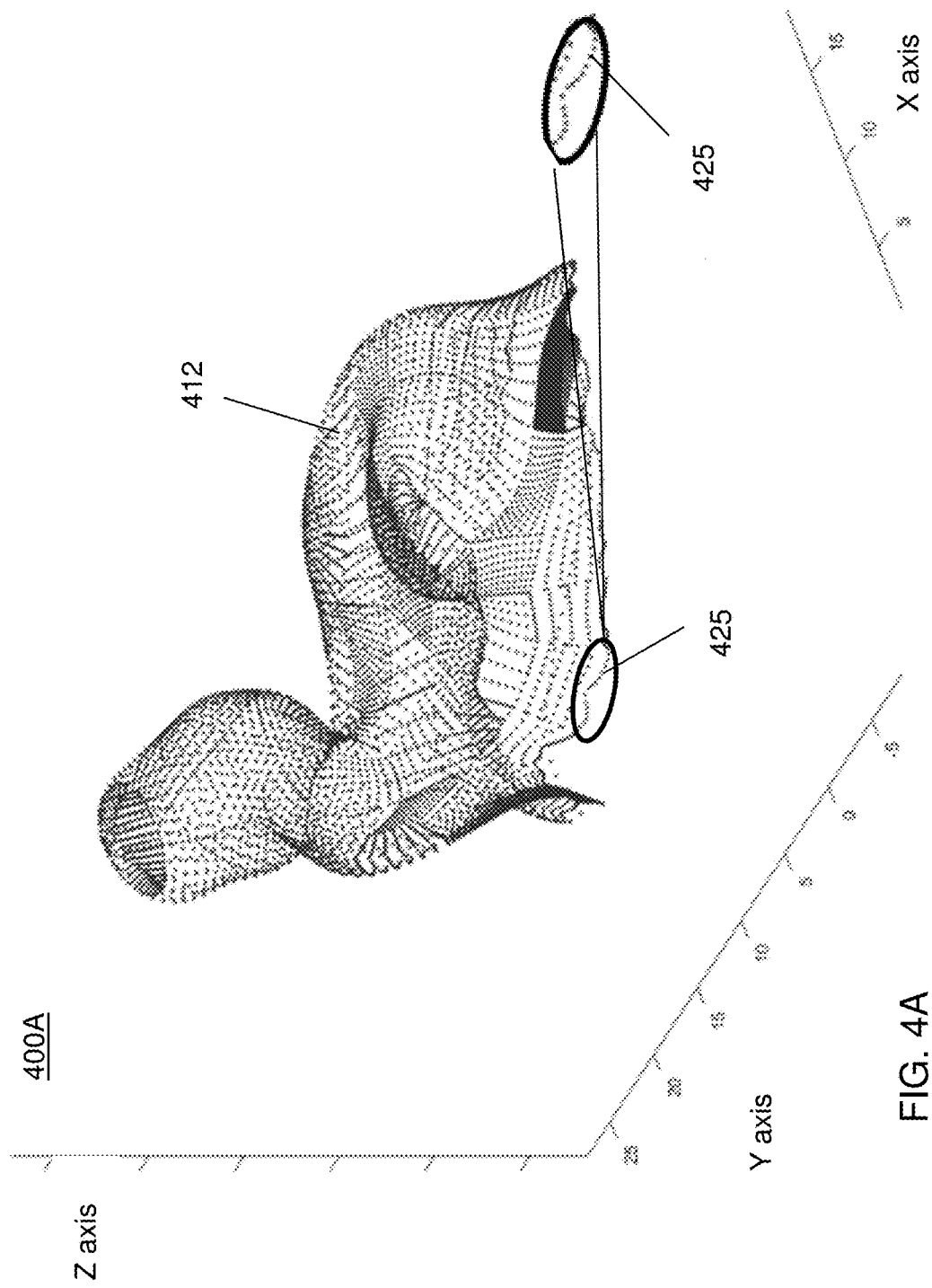
FIG. 4A illustrates an image representative of a point cloud model of the 3D digital model of the scanned ear surface of FIG. 3A.

The method 200 may, at block 204, store the vertices of the 3D digital model 300 to create a 3D point cloud model 400A (FIG. 4A). FIG. 4A illustrates an image 400A representative of a 3D point cloud model 412 of points or vertices generated from the 3D digital model 300 of the scanned ear surface of FIGS. 3A and 3B. The point cloud is defined by vertices having X, Y and Z coordinates with extrema boundary cloud points 425 located at a free end of the non-manifold 3D digital surface model. The 3D surface model is an outer boundary surface of an earpiece appliance. In FIG. 2A. the point cloud of vertices is generated by the geometry generator module 230.

The method 200 may include, at block 205, recognizing attributes and/or features by the feature recognition module 231. The features may include the auditory canal, the ear drum (canal peak), the concha, and other anatomical features of the pinna or portions of the pinna. As shown in FIG. 3A, the edge or boundary denoted by the reference numeral 360 is in close proximity to the face. The method 200 may recognize anatomical features on the 3D digital surface model. These anatomical features may include at least the canal, cymba concha, and crus of helix. The steps in block 205 thru block 208, in other embodiments, may not occur in the sequence shown in FIG. 2B.

The method 200 may include, at block 206, identifying the boundary extrema point vertices (i.e., cloud points 425) of the 3D point cloud of vertices, by the boundary locator module 232. By way of non-limiting example, boundary extrema points may be those minimum points (i.e., points 425) of the 3D point cloud model 400A with the distal end of the 3D point cloud model 400A in 3D space oriented to be the maximum point(s) of the 3D digital model. However, the minimum point may be an extrema point of the 3D point cloud model 400A. For example, as shown in FIGS. 3A and 3B, the 3D digital model 300 is oriented in three-dimensional (3D) space such that the maximum points, such as those points representative of the ear concha 310 and auditory canal 313, are those points along the 3D point cloud model represented by the distal points of the concha, auditory canal and/or closed end. The maximum points may include the surface points of surface 305 forming the model. Thereafter, the boundary extrema points may be identified along the free end of the 3D digital model. However, the minimum points and maximum points are relative terms for a frame of reference. The maximum points may be first extrema points and the minimum points may be second extrema points relative to the first extrema points of the 3D point cloud model. Thus, the method 200 determines the extrema boundary located at the free edge of a non-manifold 3D digital model surface. The steps in block 205 thru block 208, in other embodiments, may not occur in the sequence shown in FIG. 2B. The method 200 may include, at block 207, trimming the 3D digital surface model including feature peaks and base boundary extrema points as will be described in more detail in relation to FIGS. 13A and 13B. The trimming may be performed by the trimming/modifying (made-to-fit) module 233. The trimming/modifying may be performed to enhance comfort of the earplug appliance, ensure smooth transition of the earplug appliance into the canal of the ear and/or nestle of the earplug appliance such that it remains inserted within the ear. The trimming is described in more detail in relation to FIGS. 13A and 13B. The trimming may modify the canal portion of the 3D surface model surface and modify the region representative of the concha. The steps in block 205 thru block 208, in other embodiments, may not occur in the sequence shown in FIG. 2B. In some embodiments, a defined cymba concha may help retain the earpiece in the ear, but if the cymba concha peak is too pronounced, the earpiece may be uncomfortable when worn by the user. In addition, the crus of helix, may require additional cutting, trimming, or modifying to better fit the earpiece into the ear. By way of non-limiting example, if it is not enough of a valley associated with the crus of helix, the earpiece may be obstructed from being fully insertion into the ear as intended.

The method 200 may include, at block 208, generating base boundary cloud points 435 (FIG. 4B) wherein the generating includes creating, by the base boundary generator module 234, base boundary cloud points (i.e., points 435) for an earpiece appliance base mapped to the extrema boundary cloud points 425, the base boundary cloud points and the extrema boundary cloud points define vertices. The steps in block 205 thru block 208, in other embodiments, may not occur in the sequence shown in FIG. 2B. In some embodiments, generating the base boundary cloud points 435 may include generating the point locations relative to the extrema boundary cloud points 425 to generate the collection of points associated with the base boundary cloud points 435. The point locations may be a function of recognized feature found in the 3D surface model surface of the scanned data.

In some embodiments, the performance of blocks 205, 206, 207 and 208 may be performed iteratively or feature dependent.

Figure 6:
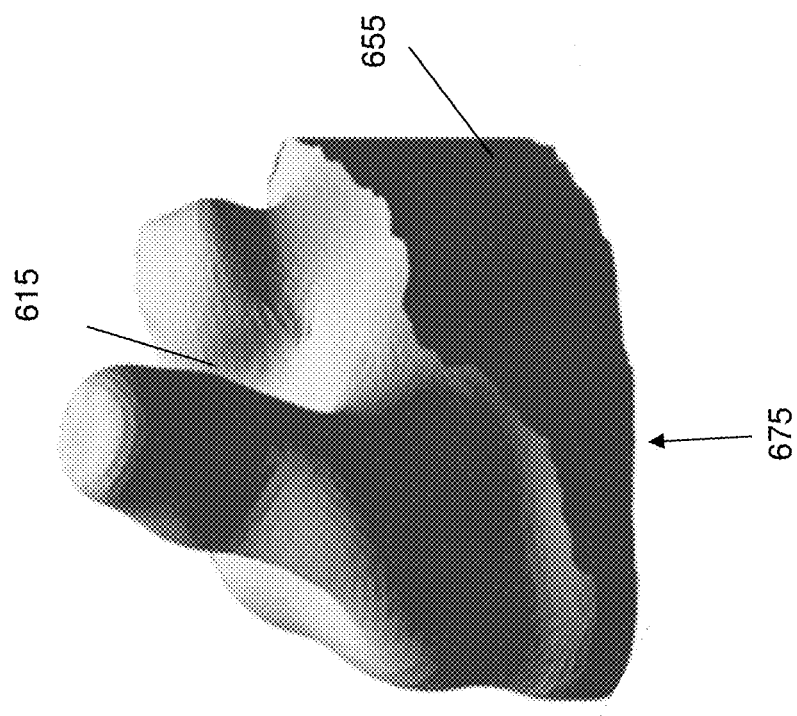
FIG. 6 illustrates an image representative of the FIG. 4B computational geometry rendered as a solid earpiece appliance with a solid base structure.

The earpiece appliance 600 may include a base extension structure 655 (FIG. 6). The base extension structure may be customized. For example, the height H (FIG. 4B) of the base relative to the boundary extrema points may be varied around the perimeter of the 3D surface model surface between the extrema boundary cloud points 425 and the base boundary cloud points 435. The base extension type may be user selected from one of feature type, active earpiece appliance, and passive earpiece appliance, as will be described in more detail later.

The method modifies the 3D surface model by creating a base boundary plane for the earpiece appliance, offset some distance from the extrema boundary, and creating a closed volume.

Figure 4B:
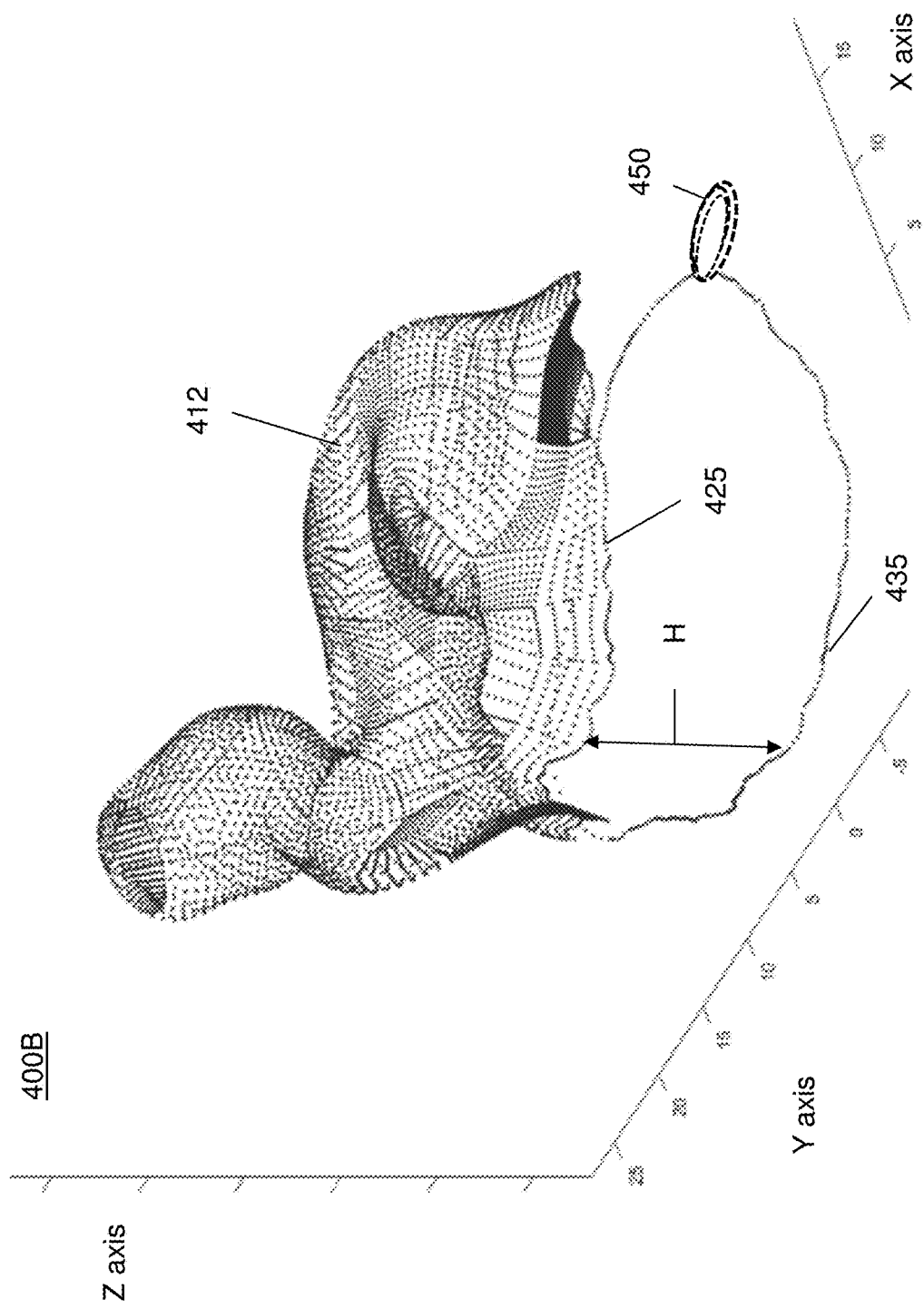
FIG. 4B illustrates an image representative of the point cloud model of FIG. 4A with the base boundary extended and the start of an external feature located.
Figure 9:
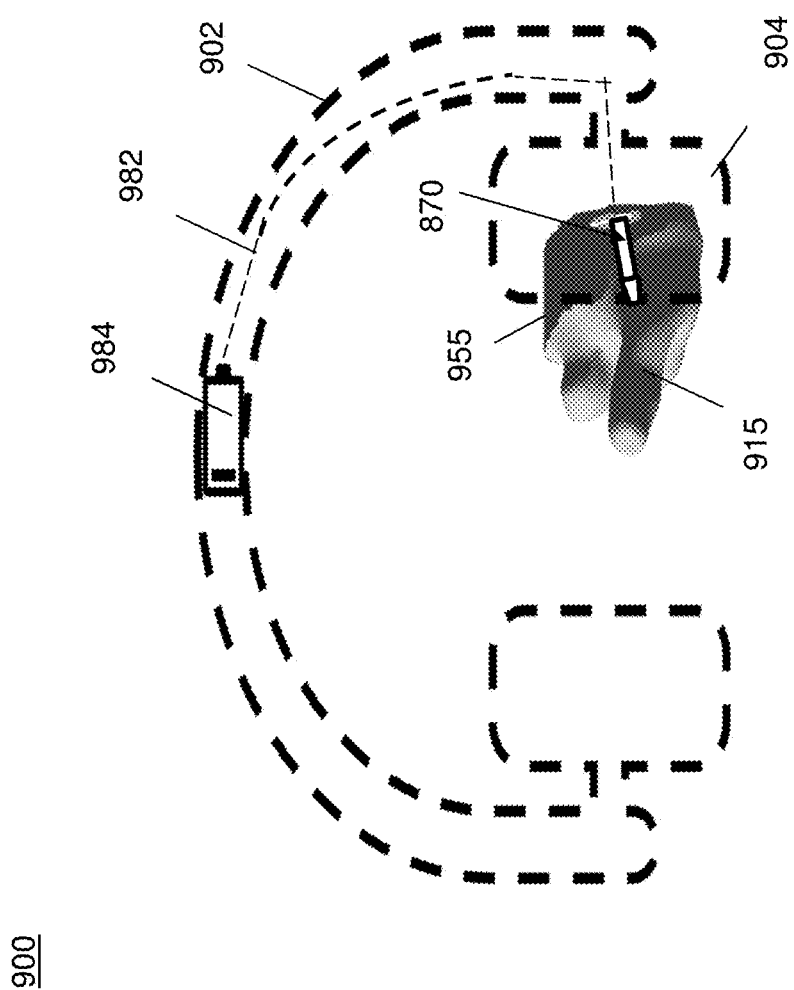
FIG. 9 illustrates an earpiece appliance kit of FIG. 8 incorporated into a headset for tethering to a user.
Figure 10:
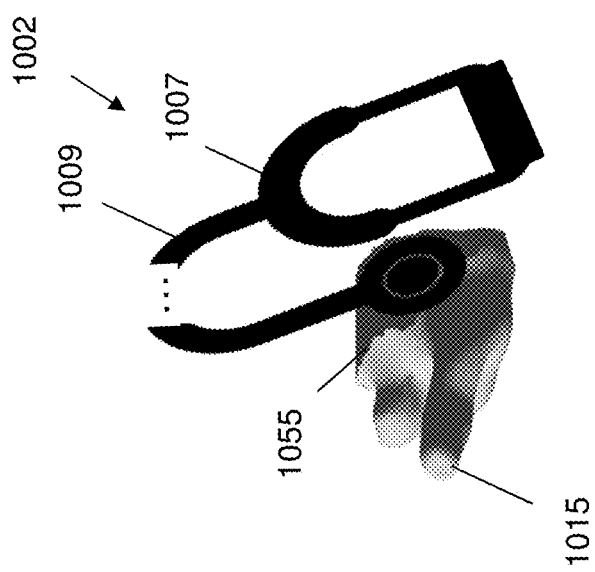
FIG. 10 illustrates an earpiece appliance kit tethered to a user via a lanyard.

The method 200 may include, at block 210, receiving an appliance type to incorporate custom base features and or appliance features. FIG. 4B illustrates an image 400B representative of the point cloud model 412 of FIG. 4A with base boundary cloud points 435 mapped and linked to the extrema point boundary 425 with an external feature (fastener) point set 450 (optional) integrated into the base extension design. In FIG. 2A, a user may select one of a hearing protection customizer module 222 or a noise reduction protection customizer module 224. The module 222 may make a passive earpiece appliance wherein the base may be customized by height and/or fastener type. The passive earpiece appliance may be tethered to a user by a lanyard or headset, for example, as shown in FIGS. 9 and 10. The module 224 allows the user to select an active earpiece appliance. The base extension of the active earpiece appliance may be varied by height based on customer needs and comfort. The base extension of the active earpiece appliance is configured to support noise reduction circuitry to be embedded within the base extension. The hearing protection customizer module 222 and/or the noise reduction protection customizer module 224 may be coupled to a feature template database 226. The feature template may include templates for adding one or more of an internal feature, an external feature and an acoustic channel(s). The feature template provides additional computational geometry data for forming in the base extension the internal feature or external feature. The internal feature may include acoustic channels which may extend into the solid 3D space of the concha and acoustic channel, for example, and to the tympanic membrane (i.e., ear drum) surface. The term tympanic membrane and ear drum will be used interchangeably herein.

Figure 4C:
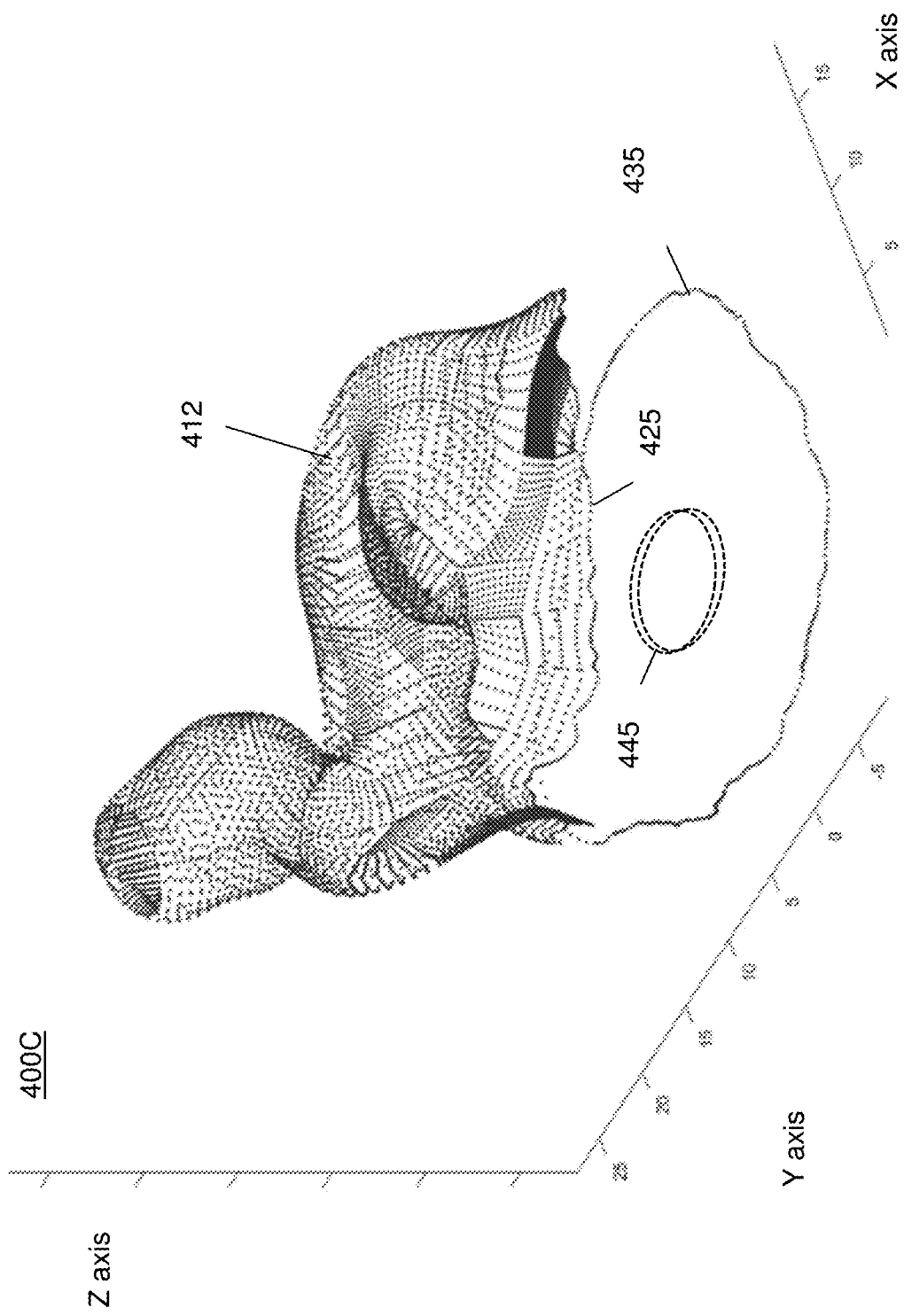
FIG. 4C illustrates an image representative of the point cloud model of FIG. 4A with the base boundary extended and the start of an internal feature located.

FIG. 4C illustrates an image 400C representative of the point cloud model 412 of FIG. 4A with a generated point base boundary cloud points 435 linked to the minimum point boundary (i.e., boundary extrema point vertices 125) and an internal feature locator, point set 445. The attachment generator module 236 may allow for integrating and/or defining the feature (fastener) type in the base extension. The point set 445 may generate a cavity or recess within the base extension. The attachment generator module 236 may include instructions for forming one or both of the external feature 750A (FIG. 7A) and internal feature 750B (FIG. 7B) in the base extension. The external feature 750A and internal feature 750B may be fastener elements for the placement/attachment of a fastener.

The method 200 may include, at block 214, importing feature template(s), adding internal and external features to the computational geometry. The generating of block 214 may be performed by the appliance geometry generator module, 238. Since the file is in a computational geometry format, Boolean operations (e.g., union, intersection, and difference) on the scan matrices and the template matrices may be used. The appliance geometry generator module, 238 may further modify the revised computational geometry data by creating an acoustic channel(s) 560C (FIG. 5C) with other internal and/or external features to create the finished computational geometry data. This may be done through the use of Boolean operations (union, intersection, and difference) with prefabricated 3D model templates from feature template database 226. Feature recognition may be used for the placement of the point set data representative of the acoustic channels to generate a path to a location in proximity to the ear drum surface in the auditory canal. The embodiments may generate one or more channels to the ear drum surface.

Figure 5A:
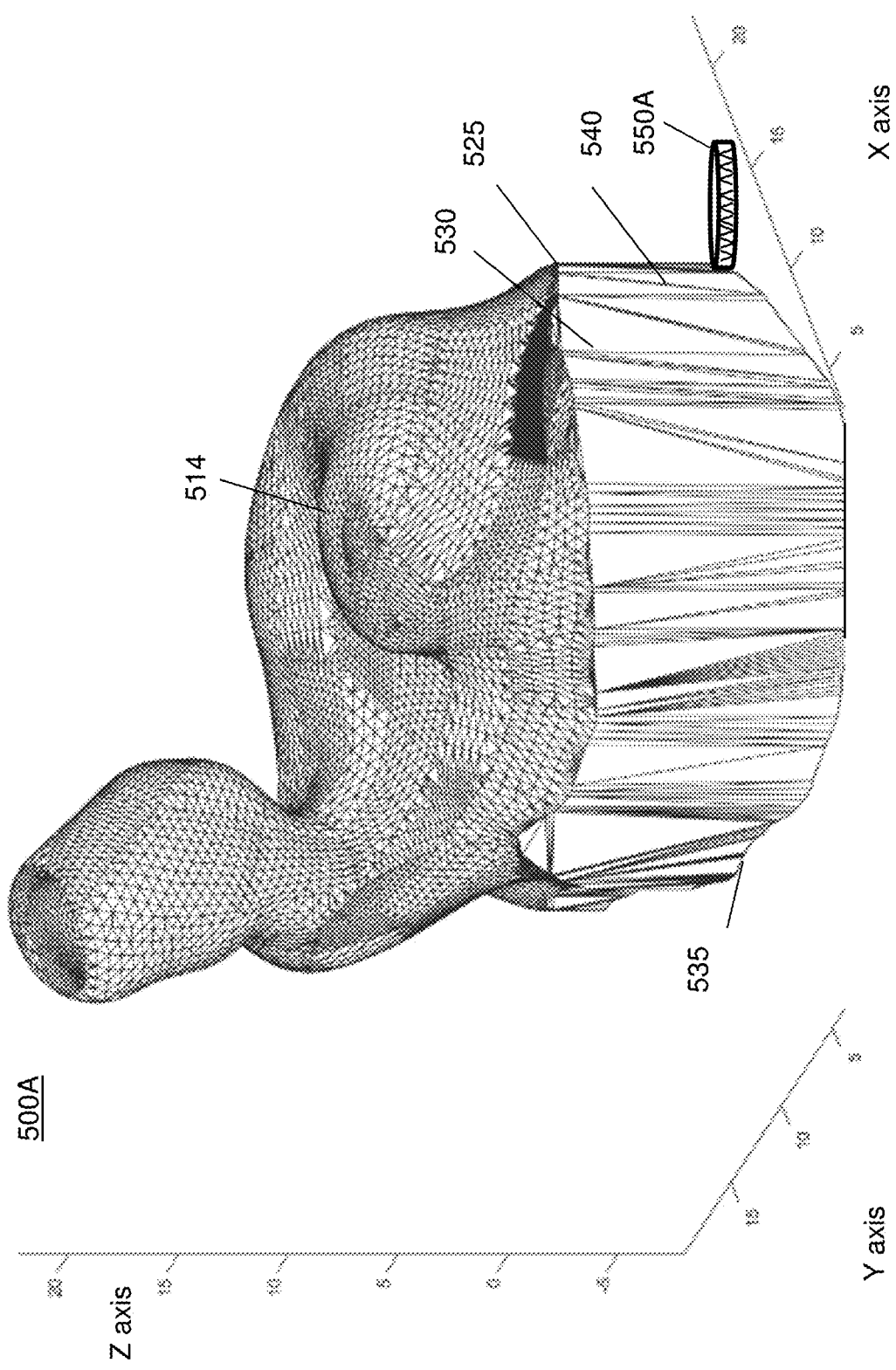
FIG. 5A illustrates an image representative of the FIG. 4B computational geometry in STL format and an external feature.

The method 200, at block 214, may include importing feature template(s) based upon the scan data attributes, 206, and user selected appliance type, 210. FIG. 5A illustrates an image 500A representative of the computational geometry volume 514 with boundary extrema 525 and 535; and base extension 540 incorporating the external feature 550A into the base extension. The feature 550A is an added tab surface extending or radiating from the bottom end of the boundary 535. External features 550A and internal features are optional.

Figure 5B:
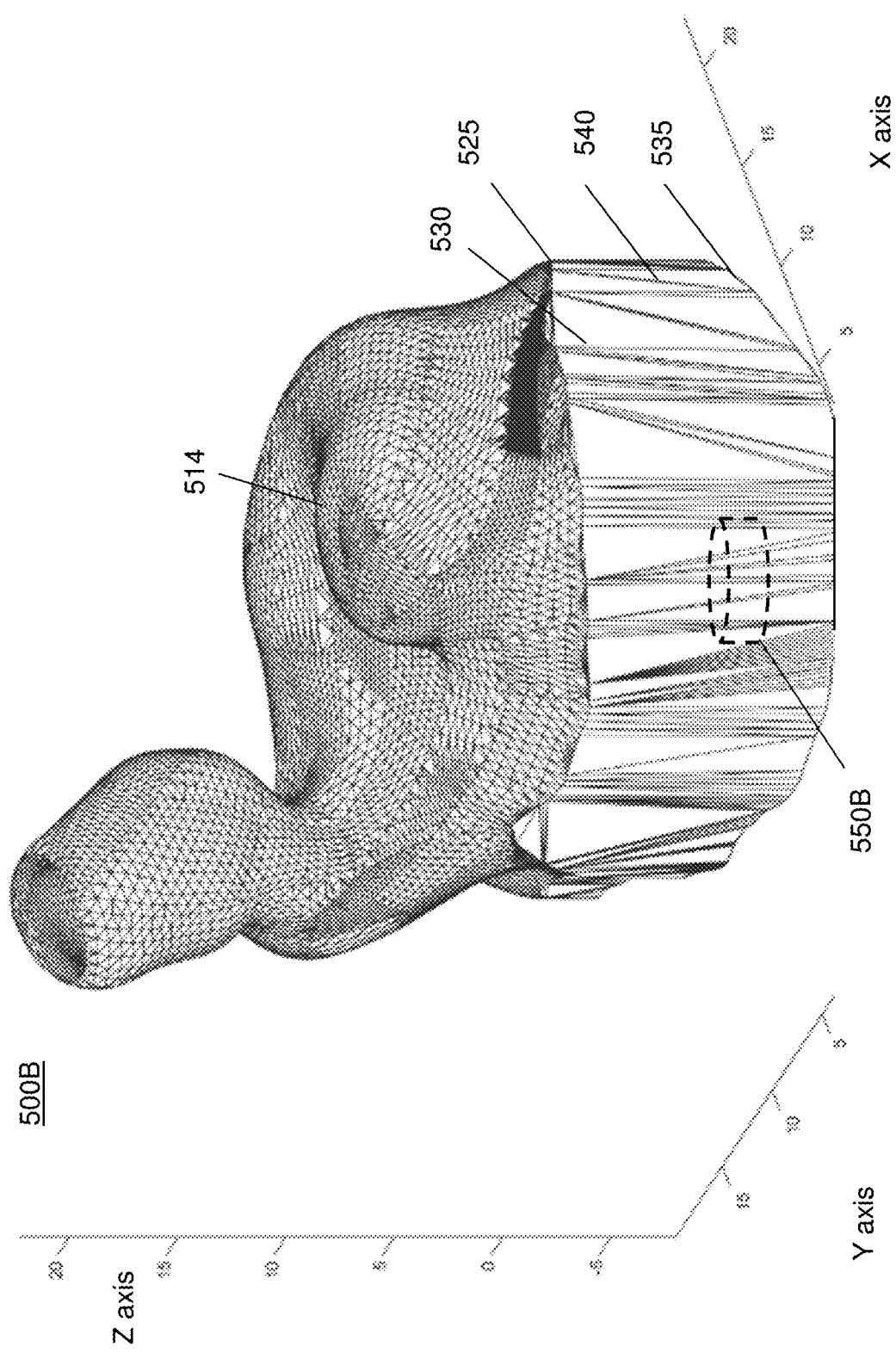
FIG. 5B illustrates an image representative of the FIG. 4C computational geometry in STL format and an internal feature.

FIG. 5B illustrates an image 500B representative of the computational geometry volume 514 with boundary extrema 525 and 535; and base extension 540 incorporating the internal feature 550B into the base extension. The feature 550B is an internal surface extending or radiating from the bottom end of the boundary 535 into the volume with positive features, for example, but not limited to, female threads, for attachment of an assembled element. An adhesive or glue may also be placed in feature 550B to fasten the assembled element.

Figure 5C:
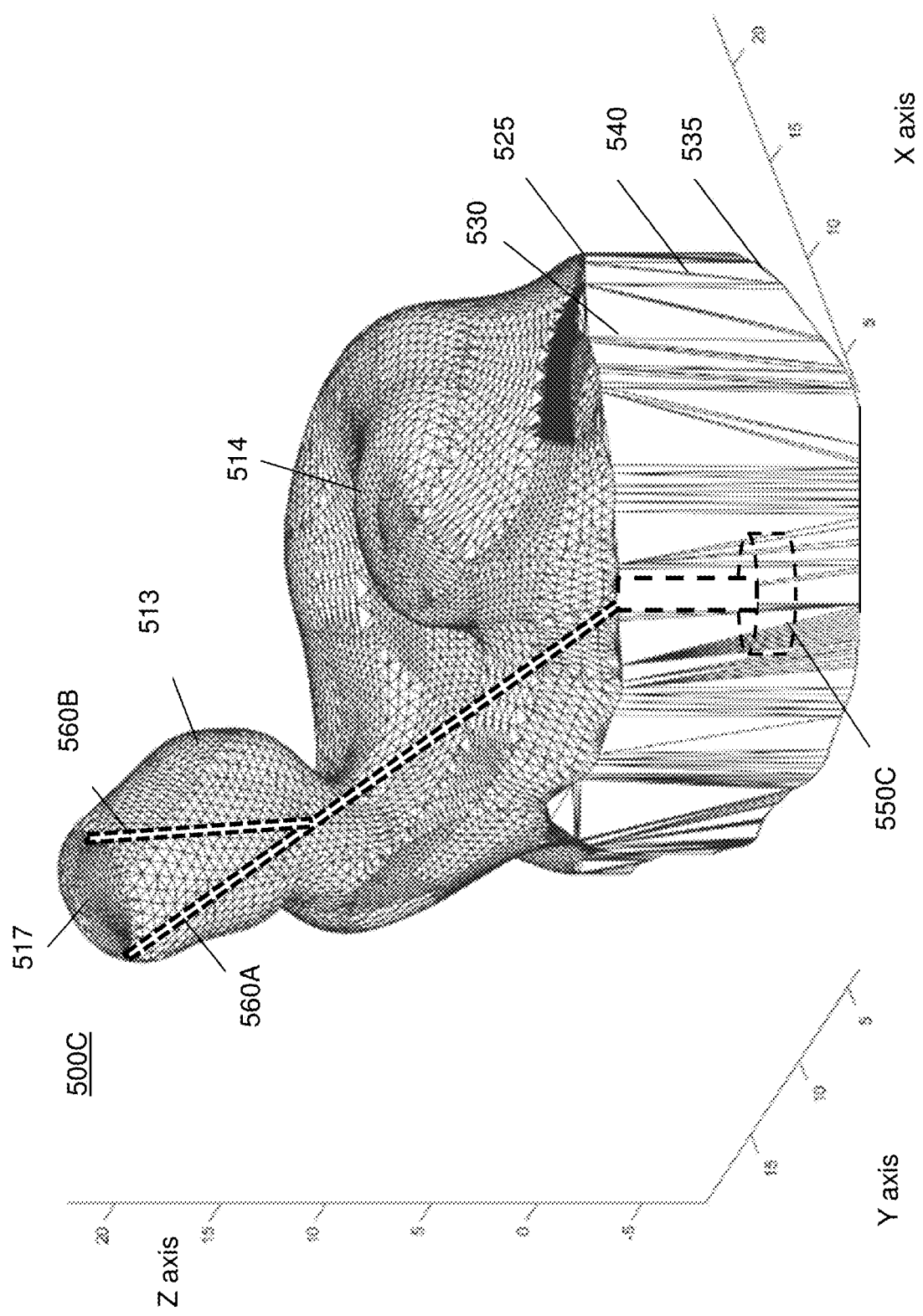
FIG. 5C illustrates an image representative of the FIG. 4C computational geometry in STL format and an internal feature with channels.

FIG. 5C illustrates an image 500C representative of the FIG. 4C computational geometry data in STL format and an internal feature 550C with acoustic channels 560A and 560B, as will be made readily apparent from the description of FIG. 8. The computational geometry data may include data representative of the ear drum surface 517 and the acoustic channel 513. The computational geometry data may be used to generate acoustic channel computational geometry data to form the acoustic channel(s) 560A and 560B. The computational geometry data may be used to form cavity computational geometry data for the generation of the cavity representative of internal feature 550C. The cavity is represented in dash lines. In some embodiments, one (first) end of the acoustic channel 560A, represented in dotted line, may be extended to the cavity of internal feature 550C so that acoustic waves originating in the cavity may propagate through the channel(s) 560A or 560B and out of the ear drum surface 517 through an opposite (second) end of the channel(s). As can be appreciated, at least one opening may be formed in the ear drum surface 517 to allow an acoustic wave to be heard by the ear of the wearer.

The method 200 may include, at block 216, generating a data file representative of a closed 3D earpiece appliance; and at block 218, causing a CAM machine 140 (FIG. 1) to manufacture a generally closed 3D earpiece appliance. FIG. 6 illustrates a rendered image 600 representative of a generally closed earpiece appliance 615 with a generally closed base extension structure 655 to be manufactured by the CAM device 140. After the earpiece appliance is manufactured, the appliance may be set to cure. In some embodiments, before providing the made-to-fit solid or generally closed earpiece appliance to the user, it may be washed or cleaned, coated with a protective layer, and/or labeled for tracking and distribution.

As shown in FIG. 6, the base extension structure 655 has varying heights relative to the actual 3D surface model. The base extension structure 655 may create, in some embodiments, a generally flat base surface 675.

FIG. 7A illustrates an image 700A representative of a solid or closed earpiece appliance 715 with a solid or closed base extension structure 755A and external feature 750A. The external feature 750A may include an eyelet or tab. In some embodiments, the tab may be punctured to form a hole therein for attaching a fastener thereto. FIG. 7B illustrates an image 700B representative of a solid or closed earpiece appliance 715 with a solid or closed base extension structure 755B and internal feature 750B. The features 750A and 750B are for illustrative purposes and should not be limiting in any way. The base extension is a solid or closed base extension structure 755A. However, in some embodiments, the solid or closed base extension structure 755A may be made of a homogeneous material which is an open or close cell structure. In some embodiments, the homogeneous material is dense.

The embodiments of FIGS. 6, 7A and 7B are representative of both a solid and closed 3D earpiece appliance. The appliance in FIG. 8 is representative of a solid 3D earpiece appliance with embedded internal (structural) features such as an acoustic channel and/or cavity. Except for the internal features and the composition of the homogeneous material, the earpiece appliance is otherwise essentially solid.

Figure 8:
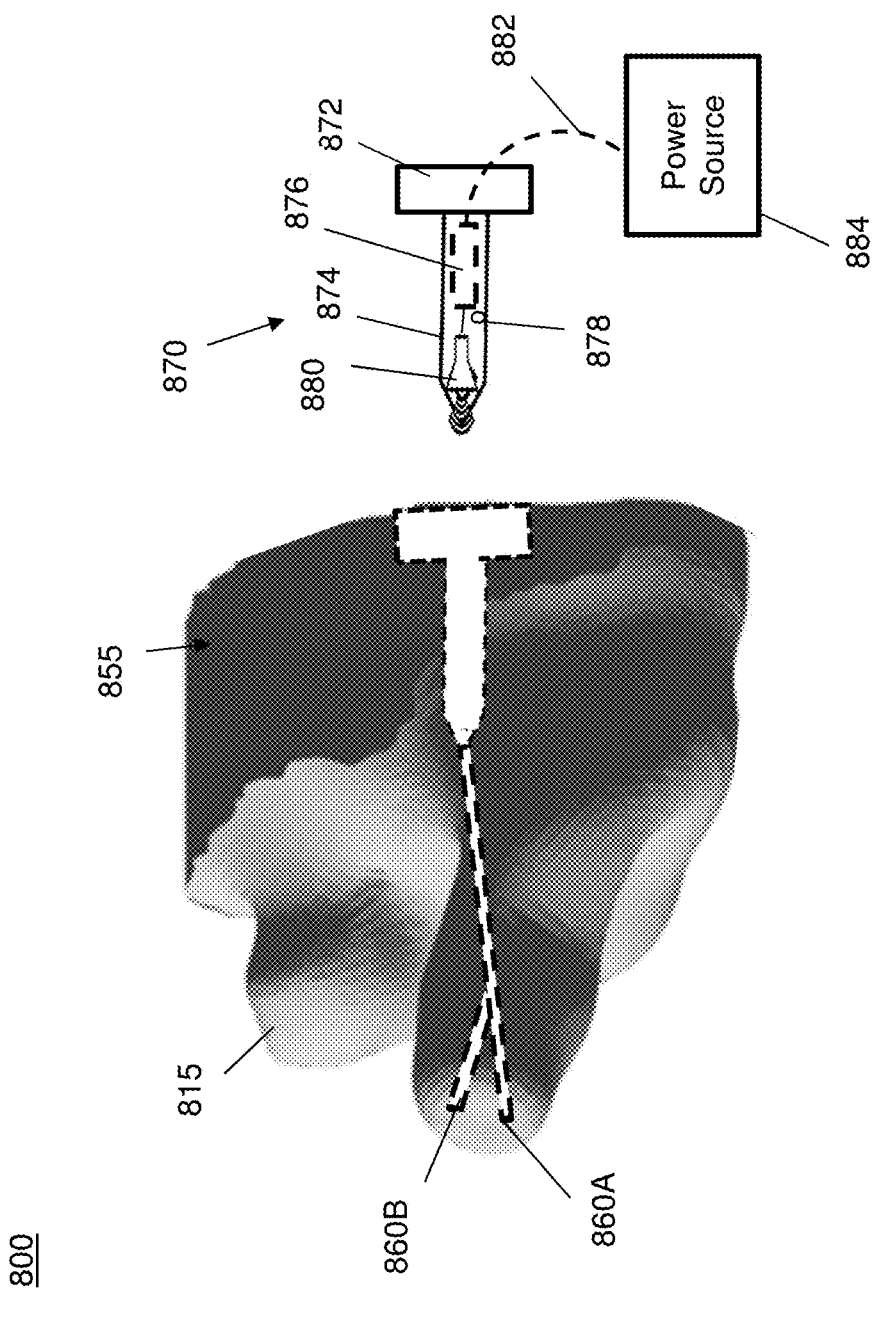
FIG. 8 illustrates an earpiece appliance kit.

FIG. 8 illustrates an earpiece appliance kit 800. The earpiece appliance kit 800 may include an earpiece appliance 815 manufactured according to the method described above in relation to FIG. 2B using system 100. The earpiece appliance kit 800 may be an active earpiece appliance kit 800. The active earpiece appliance kit 800 may include a 3D solid earpiece appliance 815 and an insertable active noise reduction device 870. By way of non-limiting example, the active noise reduction device 870 may include a housing including a barb 874 and a head 872. The barb 874 may be configured to be inserted and friction fit coupled to the solid earpiece appliance 815 and specifically, in the base extension structure 855. The active noise reduction device 870 may include noise canceling control circuitry 876. The active noise reduction device 870 may include a microphone 878 positioned in the barb 874 to capture noise in proximity to or inside of the auditory canal 12. The microphone 878 may be positioned in communication with the noise canceling control circuitry 876.

In some embodiments, the base extension structure 855 may include channels 860A and 860B for the wavelengths to propagate through the earpiece to the ear drum from the speaker. In some embodiments, the head 872 may be dimensioned to fit within and/or be recessed within the internal feature 750B (FIG. 7B). The processor further modifies the revised computational geometry by creating an acoustic channel with other internal and external features; this is done through the use of Boolean operations (union, intersection, and difference) with prefabricated 3D model templates from a feature template database. The finished computational geometry is sent to the CAM device for manufacture of the hearing protection appliance.

The active noise reduction device 870 may include a speaker 880 electrically coupled to the noise canceling control circuitry 876. The speaker 880 may be positioned in proximity to the ear drum or auditory canal and being configured to output a noise cancelling sound signal to cancel or reduce the ambient noise captured by the microphone 878. The noise canceling control circuitry 876 may include audio files (not shown), wherein one or more of the audio files may be selected to produce a noise canceling audio output or anti-noise output. The audio files may be customized for the specific work environment and expected ambient noise.

The head 872 of the noise canceling control circuitry 876 may include a wire 882 coupled to the circuitry and to an external power source 884 external to active noise reduction device 870 such that the power source 884 is configured to provide power to the speaker 880, microphone 878 and circuitry 876. In some embodiments, the head 872 may include a power contact or an internal power source.

FIG. 9 illustrates an earpiece appliance kit of FIG. 8 incorporated into a headset 902 for tethering to a user. The headset 902 may include ear pads 904 configured to have affixed the base extension structure 955 of the earpiece appliance 915. The earpiece appliance 915 may be attached to the headset pads 904 so that the earpiece appliance 915 may be inserted into the ear in the normal manner in which a headset is place about the head of a user. The external power source 984 may be coupled to or housed in the headset body. In some embodiments, the headset may include a power plug (not shown) which receives power from an external power source. In some embodiments, the headset may be part of a protective helmet. The active noise reduction device 870 is shown inserted into the base extension structure 955.

Still further the headset may include a power contact constructed and arranged to mate with the power contact of the head to supply power. The power may be communicated from power source 984 to the noise canceling control circuitry 876 via power line 982.

FIG. 10 illustrates an earpiece appliance kit 1000 tethered to a user via a lanyard 1002. The earpiece appliance 1015 may include a base extension structure 1055 which a fastener compatible with fasteners for use with a lanyard 1002. The lanyard 1002 may include a tether line 1009 having one end affixed to the earpiece appliance 1015. The lanyard 1002 may include a fastener 1007 for attachment of the lanyard 1002 to a user. By way of non-limiting example, the tether line 1009 may be a coiled and/or resilient line. In other examples, the tether line 1009 may be a flexible line. The fastener 1007 may include a loop at one end of the flexible line configured to be slipped over the head and supported about the user's neck. In other embodiments, the fastener 1007 may include a hook or loop member which can be fastened to a belt loop, belt, or other garment item.

Figure 12:
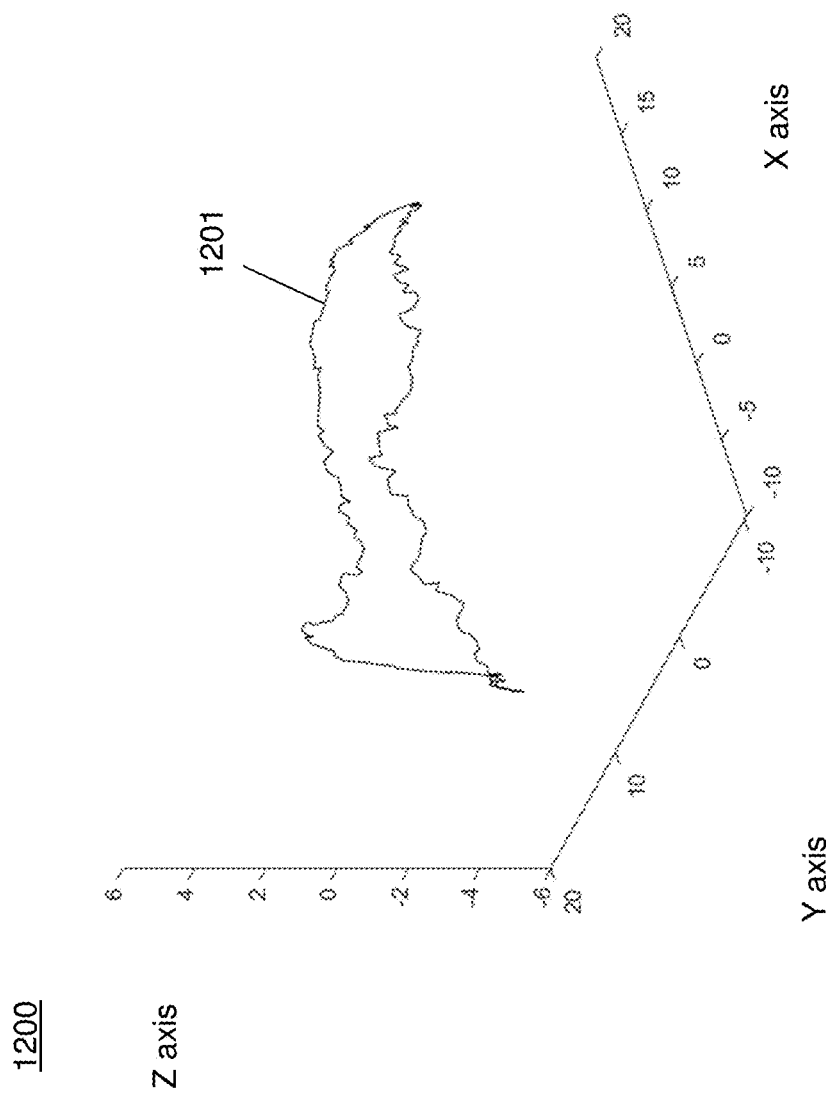
FIG. 12 illustrates the base boundary of the 3D model.

FIG. 12 illustrates an image 1200 representative of the base extrema boundary 1201 based on the extrema boundary cloud points 425 of a surface 305 (FIG. 3A).

Figure 13B:
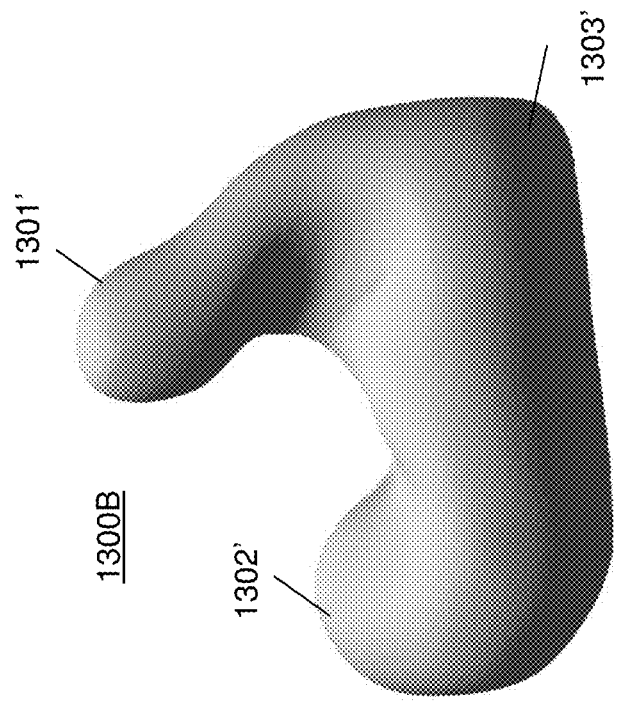
FIG. 13B illustrates a view of an image representation of a resultant digital surface model after made-to-fit trimming along the dashed lines of FIG. 13A.
Figure 13A:
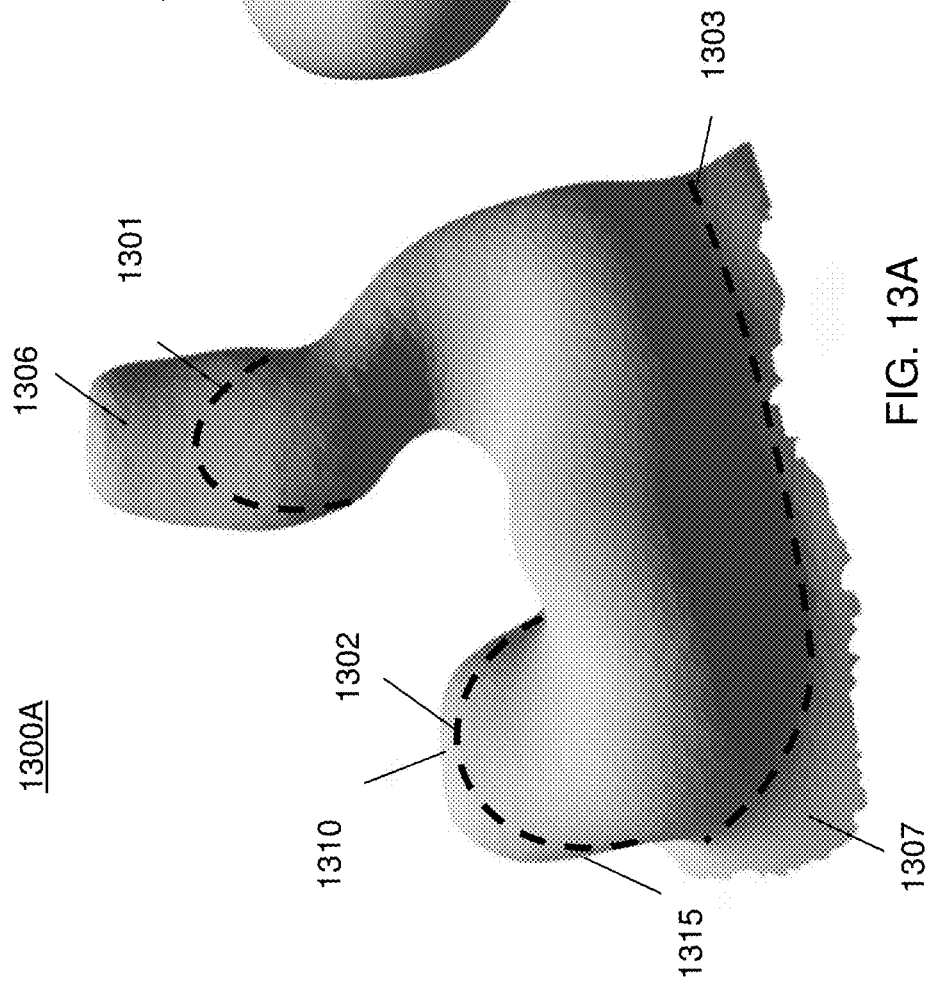
FIG. 13A illustrates a view of an image representative of a digital surface model of a scanned ear surface overlaid with dashed made-to-fit trim lines.

FIG. 13A illustrates a view of an image representative 1300A of a digital surface model of a scanned ear surface overlaid with a dashed made-to-fit trim line 1315. The made-to-fit trim line 1315 may be multiple lines 1301, 1302 and 1303 configured to reduce the outer boundary of the digital surface model. For example, the scan of the auditory canal may be bounded by the tympanic membrane, represented at reference numeral 1306. The tympanic membrane is the auditory canal peak. By way of non-limiting example, the digital surface model may be trimmed so that the resultant earplug appliance does not come in direct contact with the tympanic membrane. Hence, that surface area 1306 above line 1301 up to the eardrum or canal peak may be trimmed down to the line 1301 to form a trimmed canal peak. A closed volume would be created within the volume of the trimmed canal peak.

The digital surface model of the scanned ear surface may have a cymba concha peak denoted by the reference numeral 1310. The digital model may be trimmed to line 1302 such that the scanned surface of the cymba concha peak is trimmed to fit within the anatomical features of the concha.

The scanning of the pinna or auricle and the auditory canal may include the surface area 1307 extending beyond trim line 1303. In some embodiments, before forming the base extension structure excess surface, denoted as surface area 1307, corresponding to the inward folding surface of the helix 28 (FIG. 1) may be removed. Excess surface area 1307 may include the surface of the ear lobe (lobule), by way of non-limiting example. Excess surface area 1307 may include a portion of the helix 28 such as the outer rim (cartilage) of the ear which folds inward.

Trimming by the processor may include reducing the intrusion of the earplug appliance into auditory canal. The processor may trim the auditory canal so that a depth of insertion of the earplug appliance into the auditory canal is limited. For example, the depth of the volume of the auditory canal may be limited to extend only past a second bend of the auditory canal. The auditory canal may have varying diameters along the length thereof. The trimming of the scanned ear surface may be trimmed so the auditory canal portion of the earplug appliance can fit through the smallest diameter comfortably and/or without injuring the auditory canal when the appliance is inserted as intended.

Trimming may be performed using mathematical algorithms for smoothing and element meshing, by way of non-limiting example. The auditory canal may have a first bend and a second bend. The trimming may change concavity of the bends and monitor a normal position in medial axis of the ear. Then, the second bend may be identified as a minima.

Trimming at reference numeral 1303 is configured to provide flat build base.

Smoothing algorithms, element meshing. See triangles and reducing the growth to have a smoother contour.

FIG. 13B illustrates a view of an image representation 1300B of a resultant digital model after completing the made-to-fit trimming, by a processor, along the dashed lines of FIG. 13A. The processor executes program instruction for made-to-fit trimming. The digital image is shown as a solid volume having a trimmed cymba concha peak 1302', trimmed canal peak 1301', and a generally flat base boundary plane 1303'.

Figure 14:
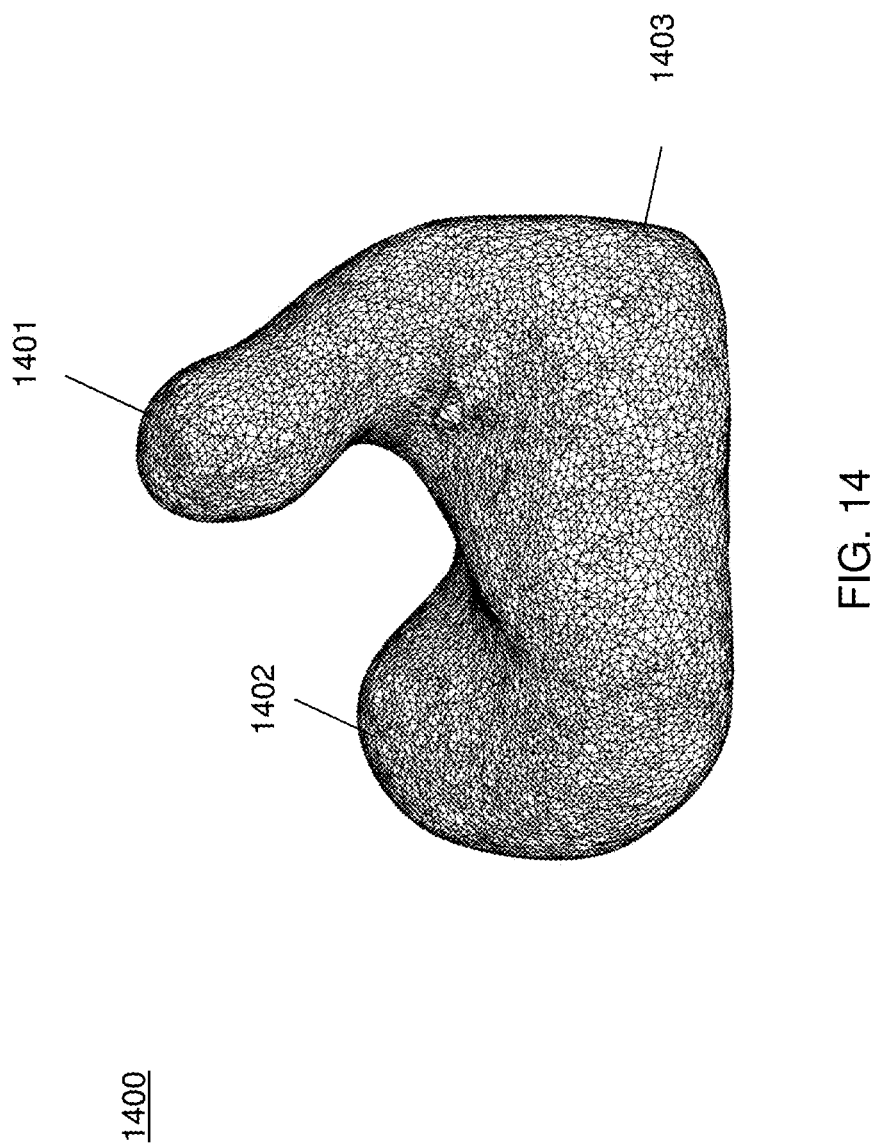
FIG. 14 illustrates a made-to-fit earplug appliance.

FIG. 14 illustrates a made-to-fit earplug appliance 1400 with a solid volume having a trimmed cymba concha peak 1402, trimmed canal peak 1401, and a base boundary plane 1403 with an added base extension structure.

Computational Hardware Overview

Figure 11:
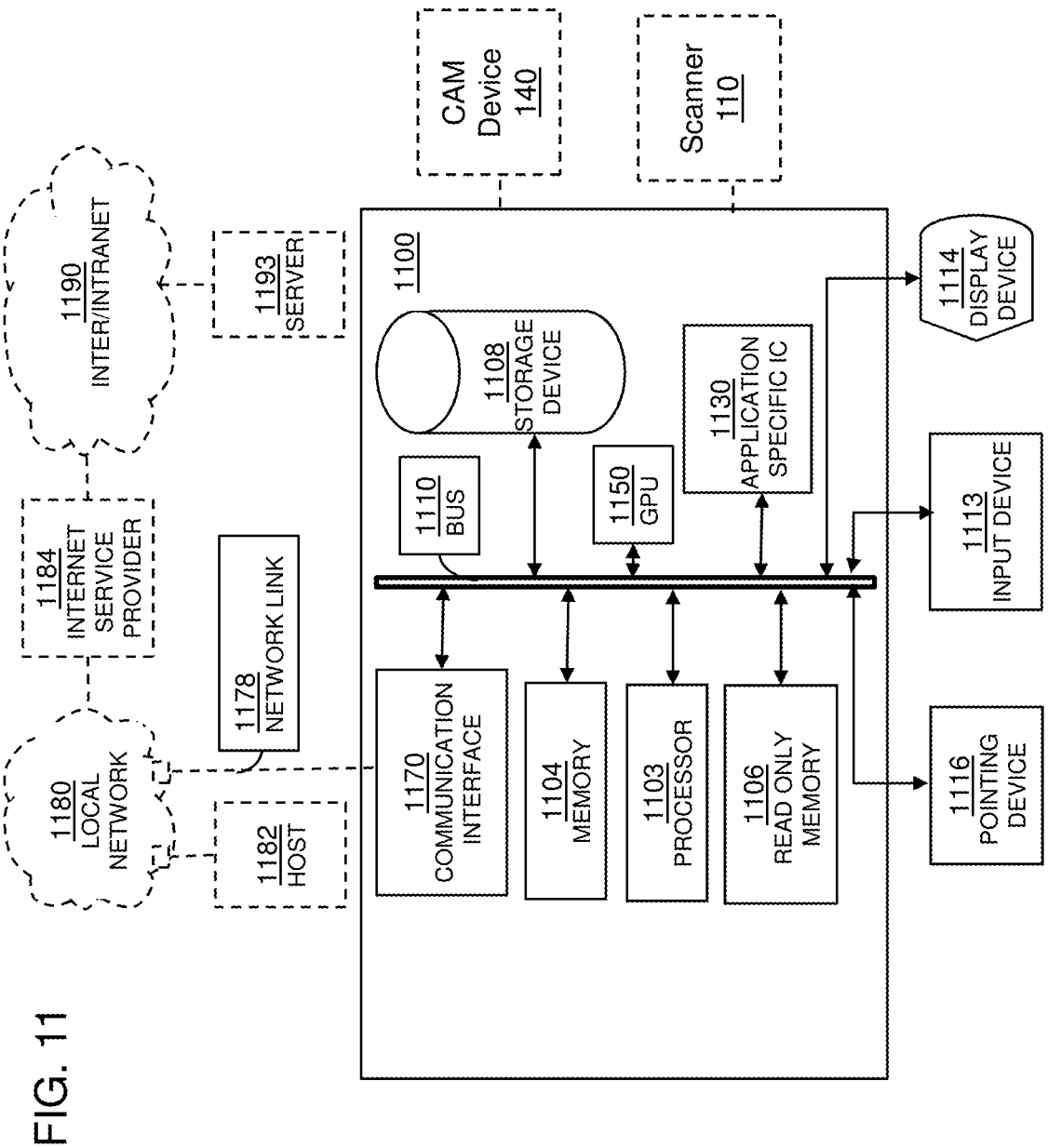
FIG. 11 illustrates a computer system.

FIG. 11 is a block diagram that illustrates a computer system 1100 (i.e., computing device 150) upon which an embodiment of the invention may be implemented or employed. The terms computing system and computer system are used interchangeably herein. Computer system 1100 includes a communication mechanism such as a bus 1110 for passing information between other internal and external components of the computer system 1100. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1100, or a portion thereof, constitutes a means for performing one or more blocks of one or more methods described herein. Thus, the computer system is a special purpose computer system.

A sequence of binary digits constitutes digital data that is used to represent a number or code for a character. A bus 1110 includes many parallel conductors of information so that information is transferred quickly among devices coupled to the bus 1110. One or more processors 1103 for processing information are coupled with the bus 1110. A processor 1103 performs a set of operations on information. The set of operations include bringing information in from the bus 1110 and placing information on the bus 1110. The set of operations also typically includes comparing two or more units of information, shifting positions of units of information, and combining two or more units of information, such as by addition or multiplication. A sequence of operations to be executed by the processor 1103 constitutes computer instructions. A graphics processing unit (GPU) 1150 may be coupled to bus 1110.

Computer system 1100 also includes a memory 1104 coupled to bus 1110. The memory 1104, such as a random access memory (RAM) or other dynamic storage device, stores information including computer instructions. The memory 1104 may also include dynamic memory which allows information stored therein to be changed by the computer system 1100. RAM allows a unit of information stored at a location called a memory address to be stored and retrieved independently of information at neighboring addresses. The memory 1104 is also used by the processor 1103 to store temporary values during execution of computer instructions. The computer system 1100 also includes a read only memory (ROM) 1106, non-volatile persistent storage device or static storage device coupled to the bus 1110 for storing static information, including instructions, that is not changed by the computer system 1100. The bus 1110 may also have coupled thereto other storage devices including a non-volatile (persistent) storage device, such as a magnetic disk or optical disk, for storing information, including instructions, that persists even when the computer system 1100 is turned off or otherwise loses power.

Information, including instructions, is provided to the bus 1110 for use by the processor from an external input device 1113, such as a keyboard containing alphanumeric keys operated by a human user, or a sensor. A sensor detects conditions in its vicinity and transforms those detections into signals compatible with the signals used to represent information in computer system 1100. Other external devices coupled to bus 1110, used primarily for interacting with humans, include a display device 1114, such as a cathode ray tube (CRT) or a liquid crystal display (LCD), light emitting diode (LED) displays, for presenting images, and a pointing device 1116, such as a mouse or a trackball or cursor direction keys, for controlling a position of a small cursor image presented on the display device 1114 and issuing commands associated with graphical elements presented on the display 1114. The processor may be coupled to peripheral devices, such as the CAM device 140, using peripheral drivers.

In the illustrated embodiment, special purpose hardware, such as an application specific integrated circuit (IC) 1130, may be coupled to bus 1110. The special purpose hardware may be configured to perform operations not performed by processor 1103 quickly enough for special purposes. Examples of application specific ICs include graphics accelerator cards for generating images for display device 1114, cryptographic boards for encrypting and decrypting messages sent over a network, speech recognition, and interfaces to special external devices, that repeatedly perform some complex sequence of operations that are more efficiently implemented in hardware.

Computer system 1100 also includes one or more instances of a communications interface 1170 coupled to bus 1110. Communication interface 1170 provides a two-way communication coupling to a variety of external devices that operate with their own processors, such as printers, scanners and external disks.

The communication interface 1170 may receive images from a scanner device 140. Pointing device 1116, input device 1113 and display device 1114 may be associated with host computer 1182.

In general, the computer system 1100 through the communication interface 1170 may be coupled with a network link 1178 that is connected to a local network 1180 to which a variety of external devices with their own processors are connected. In some embodiments, the local network 1180 may be a private network and may include wired and/or wireless communications. For example, communication interface 1170 may be a parallel port or a serial port or a universal serial bus (USB) port on a personal computer. In some embodiments, communications interface 1170 is an integrated services digital network (ISDN) card or a digital subscriber line (DSL) card or a telephone modem that provides an information communication connection to a corresponding type of telephone line. In some embodiments, a communication interface 1170 may be a cable modem that converts signals on bus 1110 into signals for a communication connection over a coaxial cable or into optical signals for a communication connection over a fiber optic cable. As another example, communications interface 1170 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1170 sends and receives electrical, acoustic or electromagnetic signals, including infrared and optical signals, that carry information streams, such as digital data.

The term computer-readable medium is used herein to refer to any medium that participates in providing information to processor 1103, including instructions for execution. Such a medium may take many forms including, but not limited to, non-volatile media, volatile media and transmission media. Non-volatile media include, for example, optical or magnetic disks, such as storage device. Volatile media include, for example, dynamic memory 1104. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1103, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1103, except for carrier waves and other signals.

Logic encoded in one or more tangible media includes one or both of processor instructions on a computer-readable storage media and special purpose hardware, such as ASIC 1130.

Network link 1178 typically provides information communication through one or more networks to other devices that use or process the information. For example, network link 1178 may provide a connection through a private or local network 1180 to a host computer 1182, such as a secure host computer. For example, in some embodiments, the pilot may be located at the host computer 1182. Thus, the user interfaces referenced in FIG. 11, may be located with the host computer 1182. The host computer 1182 may also update and/or control the EAC module 120 (application instructions) from a remote location based on earpiece design options.

In some embodiments, the computer system 1100 may connect to equipment 1184 operated by an Internet Service Provider (ISP) or Intranet Service Provider. ISP equipment 1184 in turn provides data communication services through the public, world-wide packet-switching communication network of networks now commonly referred to as the Internet 1190 or alternately over an Intranet. A computer called a server 1193 may be connected to the Internet or Intranet to provide a service in response to information received over the Internet or Intranet or provide access to external databases and/or computational resources.

The invention is related to the use of special-purpose computer system 1100 for implementing the techniques described herein. According to one embodiment of the invention, those techniques are performed by computer system 1100 in response to processor 1103 executing one or more sequences of one or more instructions contained in memory 1104 to form a computer program product. Such instructions, also called software and program code, may be read into memory 1104 from another computer-readable medium such as storage device 1108. Execution of the sequences of instructions contained in memory 1104 causes processor 1103 to perform the method blocks described herein. In alternative embodiments, hardware, such as application specific integrated circuit 1130, may be used in place of or in combination with software to implement the invention. Thus, embodiments of the invention are not limited to any specific combination of hardware and software.

Computer program code for carrying out operations described above may be written in a variety of programming languages, including but not limited to a high-level programming language, such as without limitation, C or C++, Python, Java, for development convenience. In addition, computer program code for carrying out operations of embodiments described herein may also be written in other programming languages, such as, but not limited to, interpreted languages. The program code may include hardware description language (HDL) or very high speed integrated circuit (VHSIC) hardware description language, such as for firmware programming. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed Digital Signal Processor (DSP) or microcontroller. A code in which a program of the embodiments is described can be included as a firmware in a RAM, a ROM and a flash memory. Otherwise, the code can be stored in a non-transitory, tangible computer-readable storage medium such as a magnetic tape, a flexible disc, a hard disc, a compact disc, a photo-magnetic disc, a digital versatile disc (DVD) or the like.

The signals transmitted over network link 1178 and other networks through communications interface 1170, carry information to and from computer system 1100. Computer system 1100 can send and receive information, including program code, through the networks 1180, 1190 among others, through network link 1178 and communications interface 1170. In an example using the Internet 1190, a server 1192 transmits program code for a particular application, requested by a message sent from computer 1100, through Internet 1190, ISP equipment 1184, local network 1180 and communications interface 1170. The received code may be executed by processor 1103 as it is received or may be stored in storage device 1108 or other non-volatile storage for later execution, or both. In this manner, computer system 1100 may obtain application program code in the form of a signal on a carrier wave.

Various forms of computer readable media may be involved in carrying one or more sequence of instructions or data or both to processor 1103 for execution. For example, instructions and data may initially be carried on a magnetic disk of a remote computer such as host computer 1182. The remote computer loads the instructions and data into its dynamic memory and sends the instructions and data over a telephone line using a modem. A modem local to the computer system 1100 receives the instructions and data on a telephone line and uses an infra-red transmitter to convert the instructions and data to a signal on an infra-red a carrier wave serving as the network link 1178. An infrared detector serving as communications interface 1170 receives the instructions and data carried in the infrared signal and places information representing the instructions and data onto bus 1110. Bus 1110 carries the information to memory 1104 from which processor 1103 retrieves and executes the instructions using some of the data sent with the instructions. The instructions and data received in memory 1104 may optionally be stored on storage device 1108, either before or after execution by the processor 1103.

The memory 1104 may have stored thereon applications implemented as software or computer instructions. The applications when executed by the processor 1103 may perform one or more functions and steps as described herein.

Unless otherwise defined, all terms (including technical and scientific terms) used herein have the same meaning as commonly understood by one of ordinary skill in the art to which embodiments belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In particular, unless specifically stated otherwise as apparent from the discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such data storage, transmission or display devices.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order or importance, but rather the terms first, second, etc., are used to distinguish one element from another.

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

Further, the purpose of the foregoing Abstract is to enable the U.S. Patent and Trademark Office and the public generally and especially the scientists, engineers and practitioners in the relevant art(s) who are not familiar with patent or legal terms or phraseology, to determine quickly from a cursory inspection the nature and essence of this technical disclosure. The Abstract is not intended to be limiting as to the scope of the present disclosure in any way.

Therefore, the breadth and scope of the subject matter provided herein should not be limited by any of the above explicitly described embodiments. Rather, the scope of the embodiments should be defined in accordance with the following claims and their equivalents.

We claim:

1. A system comprising:
    a scanner to scan an ear including at least an auditory canal and concha of the ear of a subject; and
    a computing device having at least one processor and tangible, non-transitory computer readable medium having program instructions which when executed to cause at least one processor to:
        receive, from the scanner, a non-manifold three-dimensional (3D) digital surface model (DSM) scan data representative of a non-manifold 3D surface model of the at least auditory canal and the concha of the ear in a computational geometry format, the 3D surface model being an outer boundary surface for an earpiece appliance;
        determine an extrema boundary located at a free edge of the non-manifold 3D surface model;
        recognize anatomical features on the non-manifold 3D surface model including a cymba concha and an auditory canal peak;
        modify the non-manifold 3D surface model relative to the recognized anatomical features by creating a base boundary plane for the earpiece appliance, offset a distance from the extrema boundary;
        create a closed volume within and between the outer boundary surface, the extrema boundary and the base boundary plane to form a digital data representation of a solid 3D earpiece appliance; and
        cause a computer-aided manufacturing (CAM) device to manufacture the solid 3D earpiece appliance based on the formed digital data representative of the solid 3D earpiece appliance.

2. The system of claim 1, wherein the program instructions which when executed by the at least one processor to further:
    determine, based on at least one user selected option, whether the earpiece appliance is a passive earpiece appliance for hearing protection or an active earpiece appliance for noise reduction, and in response to the determination, automatically selecting a design of an earpiece appliance base extension structure associated with the created closed volume within and between the extrema boundary and the base boundary plane.

3. The system of claim 1, wherein the program instructions which when executed to cause the at least one processor to further:
define heights of the base extension structure defined as a distance between the extrema boundary and the base boundary plane.

4. The system of claim 1, wherein the program instructions which when executed to cause the at least one processor to further:
integrate computational geometry data representative of at least one of a cavity, acoustic channel and fastener element into the base extension structure for the solid 3D earpiece appliance.

5. The system of claim 4, wherein the fastener element is integrated into the base extension structure and being configured to affix the solid 3D earpiece appliance to a headset.

6. The system of claim 5, further comprising:
an active noise reduction circuit having a housing configured to be inserted in the earpiece appliance base extension structure of the solid 3D earpiece appliance wherein the headset includes a power source to provide power to the noise reduction circuit.

7. The system of claim 1, wherein the program instructions which when executed to cause the at least one processor to further:
modify the recognized auditory canal peak of the non-manifold 3D surface model to reduce a height of the auditory canal peak; and
modify the recognized cymba concha by trimming the base boundary plane around the concha.

8. A method comprising:
receiving, from a scanner device, a non-manifold three-dimensional (3D) digital surface model (DSM) scan data representative of a non-manifold 3D surface model of at least an auditory canal and a concha of an ear of a subject in a computational geometry format, the 3D surface model being an outer boundary surface for an earpiece appliance;
determining an extrema boundary located at a free edge of the non-manifold 3D surface model;
recognizing anatomical features on the non-manifold 3D surface model including a cymba concha and auditory canal peak;
modifying the non-manifold 3D surface model relative to the recognized anatomical features by creating a base boundary plane for the earpiece appliance, offset a distance from the extrema boundary;
creating a closed volume within and between the outer boundary surface, the extrema boundary and the base boundary plane to form a digital data representation of a solid 3D earpiece appliance; and
causing a computer-aided manufacturing (CAM) device to manufacture the solid 3D earpiece appliance based on the formed digital data representative of the solid 3D earpiece appliance.

9. The method of claim 8, further comprising:
scanning, by the scanning device, the ear of the subject including the auditory canal and the concha to produce the 3D digital surface model scan data.

10. The method of claim 8, further comprising:
defining heights of the base extension structure defined as a distance between the extrema boundary and the base boundary plane.

11. The method of claim 8, further comprising:
integrating computational geometry data representative of at least one of a cavity, acoustic channel and fastener element into the base extension structure for the solid 3D earpiece appliance.

12. The method of claim 11, wherein the fastener element is integrated in the base extension, the fastener element being configured to affix the solid 3D earpiece appliance to a headset.

13. The method of claim 12, further comprising:
inserting an active noise reduction circuit in the base extension structure of the solid 3D earpiece appliance wherein the headset includes a power source to provide power to the noise reduction circuit.

14. The method of claim 8, further comprising:
receiving, by the CAM device, the formed data representative of the solid 3D earpiece appliance, wherein the CAM device is a 3D printer.

15. A tangible, non-transitory computer readable medium having instructions stored thereon which when executed to cause at least one processor to:
receive, from a scanner, a non-manifold three-dimensional (3D) digital surface model (DSM) scan data representative of a non-manifold 3D surface model of at least an auditory canal and a concha of an ear of a subject in a computational geometry format, the 3D surface model being an outer boundary surface for an earpiece appliance;
determine an extrema boundary located at a free edge of the non-manifold 3D surface model;
recognize anatomical features on the non-manifold 3D surface model including a cymba concha and auditory canal peak;
modify the non-manifold 3D surface model relative to the recognized anatomical features by creating a base boundary plane for the earpiece appliance, offset a distance from the extrema boundary;
create a closed volume within and between the outer boundary surface, the extrema boundary and the base boundary plane to form a digital data representation of a solid 3D earpiece appliance; and
cause a computer-aided manufacturing (CAM) device to manufacture the solid 3D earpiece appliance based on the formed digital data representative of the solid 3D earpiece appliance.

16. The tangible, non-transitory computer readable medium of claim 15, wherein the instructions to create of the base boundary, further comprising instructions which when executed to cause at least one processor to:
define heights of the base extension structure defined as a distance between the extrema boundary and the base boundary plane.

17. The tangible, non-transitory computer readable medium of claim 15, wherein instructions to create of the base boundary, further comprising instructions which when executed to cause at least one processor to:
integrate computational geometry data representative of at least one of a cavity, acoustic channel and fastener element into the base extension structure for the solid 3D earpiece appliance.

18. The tangible, non-transitory computer readable medium of claim 17, wherein the fastener element is integrated in the base extension structure and the fastener element is configured to affix the solid 3D earpiece appliance to a headset.

19. The tangible, non-transitory computer readable medium of claim 15, further comprising instructions which when executed to cause the at least one processor to:
    send the formed data representative of the solid 3D earpiece appliance to the CAM device, wherein the CAM device is a 3D printer.

\* \* \* \* \*